United States Patent
Rea et al.

(10) Patent No.: US 12,377,544 B2
(45) Date of Patent: Aug. 5, 2025

(54) REDUNDANT ROBOT POWER AND COMMUNICATION ARCHITECTURE

(71) Applicant: Verb Surgical Inc., Santa Clara, CA (US)

(72) Inventors: Rochelle Rea, San Leandro, CA (US); Klaus Zietlow, Piedmont, CA (US); Adam Hoffman, San Jose, CA (US); Yiqi Zeng, San Jose, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

(21) Appl. No.: 18/668,858

(22) Filed: May 20, 2024

(65) Prior Publication Data

US 2024/0308075 A1     Sep. 19, 2024

Related U.S. Application Data

(63) Continuation of application No. 18/306,857, filed on Apr. 25, 2023, now Pat. No. 12,005,589, which is a
(Continued)

(51) Int. Cl.
*H02H 7/085* (2006.01)
*A61B 34/30* (2016.01)
(Continued)

(52) U.S. Cl.
CPC ............ *B25J 9/1682* (2013.01); *A61B 34/30* (2016.02); *B25J 9/0084* (2013.01); *B25J 9/161* (2013.01);
(Continued)

(58) Field of Classification Search
CPC ............ A61B 2090/0818; A61B 34/30; A61B 2017/00477; A61B 2017/00734;
(Continued)

(56) References Cited

U.S. PATENT DOCUMENTS

2006/0149418 A1    7/2006  Anvari
2008/0144245 A1    6/2008  Fuchik et al.
(Continued)

FOREIGN PATENT DOCUMENTS

FR    2778551 A1    11/1999
WO    2018/118486 A2    6/2018

OTHER PUBLICATIONS

International Preliminary Report on Patentability for PCT/US2021/021599 mailed Sep. 22, 2022, 11 pages.
(Continued)

*Primary Examiner* — Bryan R Perez
(74) *Attorney, Agent, or Firm* — Aikin & Gallant, LLP

(57) ABSTRACT

An electronic circuit for a surgical robotic system includes a central power node, a first voltage bus that electrically couples a first power source to the node, a second voltage bus that electrically couples a second power source to the node, and several robotic arms, each arm is electrically coupled to the node via an output circuit breaker and is arranged to draw power from the node. Each bus is arranged to provide power from a respective power source to the node and each bus has an input circuit breaker that is arranged to limit a first output current flow from the node and into the bus. Each breaker that is arranged to limit a second output current flow from the node and into a respective arm. A breaker is arranged to open in response to a fault occurring within the respective arm, while the other breakers remain closed.

20 Claims, 11 Drawing Sheets

Related U.S. Application Data continuation of application No. 16/816,055, filed on Mar. 11, 2020, now Pat. No. 11,673,274.

(51) Int. Cl.
 *B25J 9/00* (2006.01)
 *B25J 9/16* (2006.01)
 *H02H 7/00* (2006.01)
 *A61B 17/00* (2006.01)

(52) U.S. Cl.
 CPC ............ *H02H 7/00* (2013.01); *H02H 7/0856* (2013.01); *A61B 2017/00477* (2013.01)

(58) Field of Classification Search
 CPC ... A61B 2090/571; A61B 90/03; A61B 34/37; B25J 19/066; B25J 9/1682; B25J 9/0084; B25J 9/161; B25J 9/1674; B25J 19/005; H02H 7/262; H02H 7/22; H02H 3/021; H02H 3/087; H02J 1/102; H02J 9/062
 See application file for complete search history.

(56) References Cited

U.S. PATENT DOCUMENTS

| | | |
|---|---|---|
| 2015/0112481 A1 | 4/2015 | Burns et al. |
| 2017/0277607 A1 | 9/2017 | Samii et al. |
| 2018/0185208 A1 | 7/2018 | Jnsson et al. |
| 2019/0044372 A1* | 2/2019 | Cochran ................. H02J 9/061 |
| 2019/0201042 A1* | 7/2019 | Nott ....................... A61B 34/76 |

OTHER PUBLICATIONS

International Search Report and Written Opinion of the International Searching Authority dated Jun. 28, 2021 for related International Application No. PCT/US2021/021599.

* cited by examiner

REDUNDANT ROBOT POWER AND COMMUNICATION ARCHITECTURE

CROSS-REFERENCE TO RELATED APPLICATION

This application is a continuation of U.S. patent application Ser. No. 18/306,857, filed Apr. 25, 2023, entitled "REDUNDANT ROBOT POWER AND COMMUNICATION ARCHITECTURE," which is a continuation of U.S. patent application Ser. No. 16/816,055, filed Mar. 11, 2020, now U.S. Pat. No. 11,673,274, issued Jun. 13, 2023, which are incorporated herein by reference.

FIELD

An embodiment of the disclosure relates generally to surgical robotic systems, and more specifically to the power and communication architecture of such systems. Other embodiments are also described.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one camera through the incisions into the patient. The surgical procedures can then be performed by using the introduced surgical tools, with the visualization aid provided by the camera.

Generally, MIS provides multiple benefits, such as reduced patient scarring, less patient pain, shorter patient recovery periods, and lower medical treatment costs associated with patient recovery. MIS can be performed with surgical robotic systems that include one or more robotic arms for manipulating surgical tools based on commands from a remote operator. A robotic arm may, for example, support at its distal end various devices such as surgical end effectors, imaging devices, cannulas for providing access to the patient's body cavity and organs, etc. Thus, a surgical robotic arm can assist in performing surgery.

Control of such robotic systems may require control inputs from a user (e.g., surgeon or other operator) via one or more user interface devices that translate manipulations or commands from the user into control of the robotic system. For example, in response to user commands, a tool driver having one or more motors may actuate one or more degrees of freedom of a surgical tool when the surgical tool is positioned at the surgical site in the patient.

SUMMARY

In some cases, surgical robotic arms of a surgical robotic system are heavy and cumbersome for someone to carry. For instance, the arms may include several components, such as actuators and motors that enable the arms to have several degrees of freedom, and may be made of sturdy material that is heavy, such as metal. Since the arms cannot be easily moved, the arms may be mounted upon a surgical table that is itself mounted to a floor of an operating room in order to support the arms. Along with the arms, the surgical table may include table-side electronics that powers and controls both the arms and the surgical table. Specifically, the system may include a control computer (which may be located within the operating room) that receives commands from (a host computer of) the operator, translates the commands into robotic control commands, and transmits the robotic control commands to the table-side electronics, which then routes the control commands to the arms in order to cause the arms to move according to the commands.

During surgery, a patient is laid upon the surgical table and the robotic arms may hang over the patient while the operator (e.g., a surgeon) manipulates surgical tools that are supported or coupled at distal ends of the robotic arms. If a fault occurs within the system during surgery, the surgical arms may be rendered unmovable and potentially cage the patient on the surgical table. For example, a fault may occur in the event of a communication failure between the table-side electronics and the host computer. As another example, a component (e.g., a communication controller) of the table-side electronics that enables communication with the host computer may unexpectedly fail. With the communication interrupted, the table-side electronics would not receive robotic control commands, and therefore actuators and motors within the arms that enable movement may be rendered inoperable. In order to avoid caging the patient by the inoperable robotic arms, conventional systems may include mechanical bailouts which when used allow the arms to be removed from the table, and thusly freeing the patient. Physically removing an arm from the table, however, is not preferable because a user may accidentally drop the arm on top the patient, thereby causing injury. Therefore, there is a need for a fault-safe redundant robot power and communication architecture that provides power and communication to the arms and table in order to avoid caging the patient during instances in which a fault occurs, thereby alleviating the need for mechanical bailouts.

The present disclosure provides a fault-safe surgical robotic system with table-side electronics that includes a first communication controller, a second communication controller, and a monitoring controller that provide communication redundancies to ensure that no single failure (or fault) within the (communication) system may render the robotic arms and/or surgical table completely inoperable during a surgical procedure. To accomplish this, one of the communication controllers (e.g., the first controller) perform communication operations, while the other communication controller (e.g., the second controller) is a redundant controller and therefore is available in case of a fault within the first controller. For example, both communication controllers may receive, from a host, an instruction to drive a robotic arm to perform a movement. Specifically, the instruction is received by the communication controllers from the control computer that translates the instruction as a robotic control command. The first controller, however, may have a master responsibility that includes communicating with the robotic arm and the host (via the control computer). For instance, the first controller may route (e.g., re-packetize and transmit) the robotic control command to the robotic arm as a joint control signal. The joint control signal may cause an actuator or motor within the arm to change positions.

The communication architecture is redundant, such that the second communication controller may perform at least some of the operations of the first communication controller, and in response to detecting a fault may take over the master responsibility. For instance, the second controller may also re-packetize the robotic control command as another joint control signal, but may not transmit the signal to the arm since the first controller has the master responsibility. During the surgical procedure, the monitoring controller may detect a fault within the system, or more specifically within the first controller. To detect the fault, the monitoring controller may monitor output data of the first controller to determine whether the data is inconsistent with the (e.g., instruction contained within the) robotic control command. In response to detecting a fault, the monitoring controller signals that the second controller is to have the master responsibility instead of the first controller. As a result, the second controller may begin routing data (e.g., joint control signals) to the arms in order to facilitate arm movement instead of the first controller. Thus, the surgical robotic system may continue to operate using the second redundant communication controller, even in the occurrence of a fault within system.

In one embodiment, the surgical robotic system may include a redundant power architecture that enables the components (e.g., the robotic arms and the surgical table) of the surgical robotic system to operate in case of a power fault, such as a short. Specifically, the system may implement redundant power sources, such as an Alternating Current (AC) mains power supply and a battery that are both arranged to provide power on separate power busses. The system may include several circuit breakers at different locations along each of the power busses that are controlled by one or more power controllers. If a fault occurs, the controllers may active an appropriate circuit breaker in order to isolate the fault, which ensuring that the remainder of the system continues to have access to power.

According to another embodiment, the surgical robotic system may allow a user (e.g., a medical professional) within an operating room to adjust a position of a robotic arm in cases in which a (e.g., communication) fault occurs, such as when communication with the host is abruptly terminated. Specifically, the system may be able to operate in one of two modes at any given time. A first mode is a "teleoperation" mode in which the table-electronics (e.g., at least one of the first and second controllers) is in communication with the host. For instance, the table-side electronics may establish, via the control computer, communication (e.g., via a communication link) with the host by receiving robotic control commands that are translated by the control computer from commands the control computer receives from the host. Each of the robotic control commands may be for instructing one of the robotic arms to perform a movement. Each of the arms may have a user-actuated switch that when actuated by a user enables the robotic arm to be moved (e.g., repositioned while still mounted on the surgical table) by the user. Once the communication is established, however, the user-actuated switch is overridden thereby preventing the switch from enabling the robotic arm to move. The system prevents the switch from allowing the user to move the arm since the host or operator is controlling the arm. The system is able to determine that communication with the host has ceased. For example, the table-side electronics may cease receiving commands from the host, via the control computer. In response to determining that communication with the host (and/or the control computer) is lost or has been terminated, the system enters a second mode or "local control" mode which allows the user-actuated switch to enable the robotic arm to move when actuated by the user. Thus, in cases in which communication is lost and as a result surgery being performed upon a patient may no longer be performed by the surgical robotic system, the medical professionals within the operating room may move the robotic arms in order to move the patient to a more conventional operating room setting. Or, rather than move the patient, the robotic arms may be moved in order to allow a surgeon who is physically present within the operating room to access the patient in order to complete the operation.

The above summary does not include an exhaustive list of all embodiments of the disclosure. It is contemplated that the disclosure includes all systems and methods that can be practiced from all suitable combinations of the various embodiments summarized above, as well as those disclosed in the Detailed Description below and particularly pointed out in the claims. Such combinations may have particular advantages not specifically recited in the above summary.

BRIEF DESCRIPTION OF THE DRAWINGS

The embodiments are illustrated by way of example and not by way of limitation in the figures of the accompanying drawings in which like references indicate similar elements. It should be noted that references to "an" or "one" embodiment of this disclosure are not necessarily to the same embodiment, and they mean at least one. Also, in the interest of conciseness and reducing the total number of figures, a given figure may be used to illustrate the features of more than one embodiment, and not all elements in the figure may be required for a given embodiment.

DETAILED DESCRIPTION

Several embodiments of the disclosure with reference to the appended drawings are now explained. Whenever the shapes, relative positions and other embodiments of the parts described in a given embodiment are not explicitly defined, the scope of the disclosure here is not limited only to the parts shown, which are meant merely for the purpose of illustration. Also, while numerous details are set forth, it is understood that some embodiments may be practiced without these details. In other instances, well-known circuits, structures, and techniques have not been shown in detail so as not to obscure the understanding of this description. Furthermore, unless the meaning is clearly to the contrary, all ranges set forth herein are deemed to be inclusive of each range's endpoints.

Figure 1:
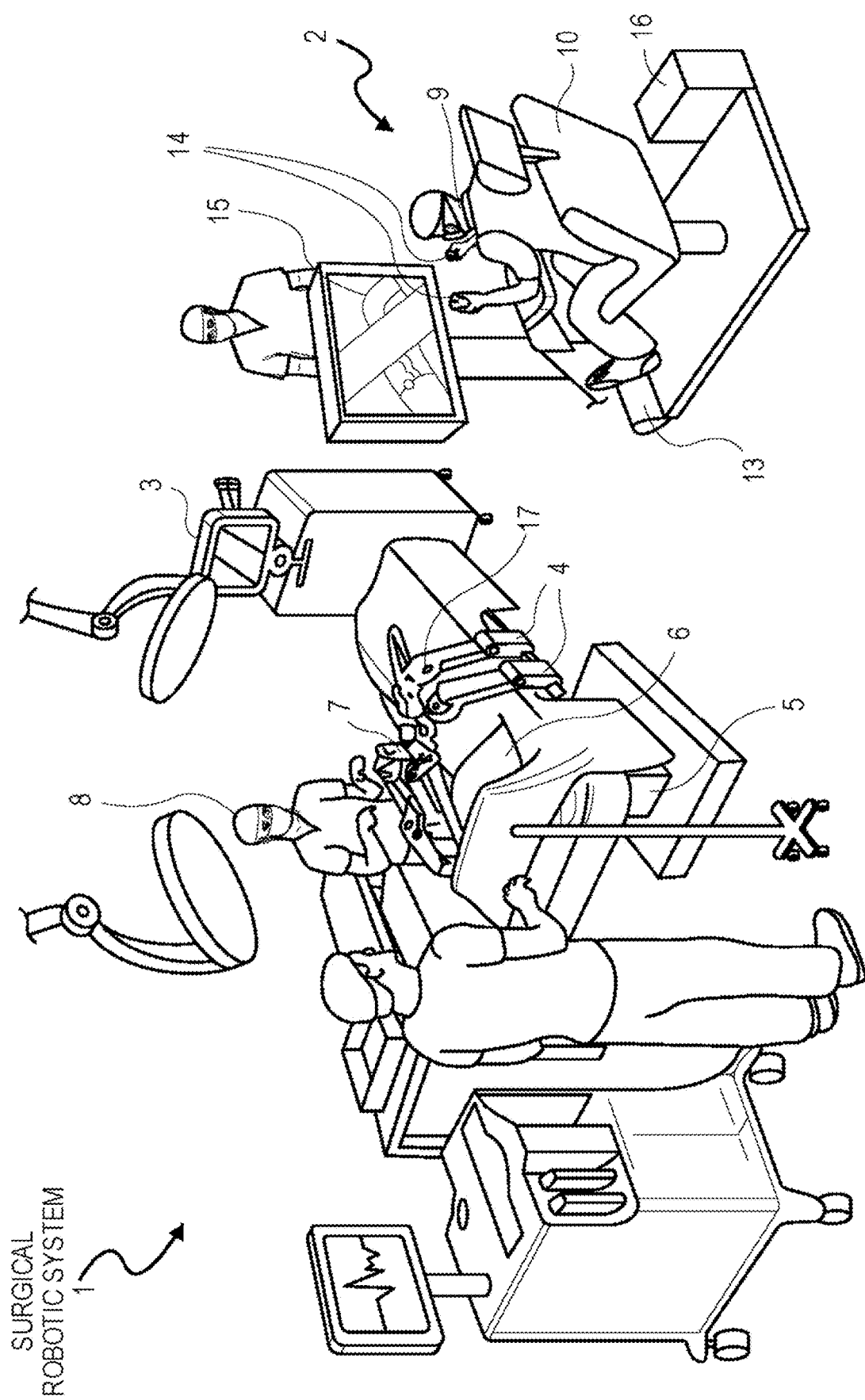
FIG. 1 shows a pictorial view of an example surgical robotic system in an operating arena.

FIG. 1 shows a pictorial view of an example surgical robotic system 1 in an operating arena. The robotic system 1 includes a user console 2, a control computer (or tower) 3, and one or more surgical robotic arms 4 at a surgical robotic table (or surgical table) 5. In one embodiment, the arms 4 may be mounted to a table or bed on which the patient rests as shown in the example of FIG. 1, or they may be mounted to a cart separate from the table or bed. In one embodiment, at least some of the arms 4 may be configured differently. For example, at least some of the arms may be mounted on a ceiling, sidewall, or in another suitable structural support. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices (handheld UIDs) 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4).

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site). Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 (or driving mechanism) in the robotic system 1. The UID 14 may be communicatively coupled to the rest of the robotic system 1, e.g., via a console computer system 16 (or host). The UID 14 can generate spatial state signals corresponding to movement of the UID 14, e.g., position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 or driving mechanism may include one or more actuators and/or one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6.

In some embodiments, the communication between the surgical robotic table 5 and the user console 2 may be through a control computer 3, which may translate user commands that are received from the user console 2 (and more particularly from the console computer system 16) into robotic control commands that transmitted to the arms 4 on the surgical table 5. The control computer 3 may also transmit status and feedback from the surgical table 5 back to the user console 2. The communication connections between the surgical table 5, the user console 2, and the control computer 3 may be via wired (e.g., optical fiber) and/or wireless links, using any suitable ones of a variety of data communication protocols, such as BLUETOOTH protocol. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
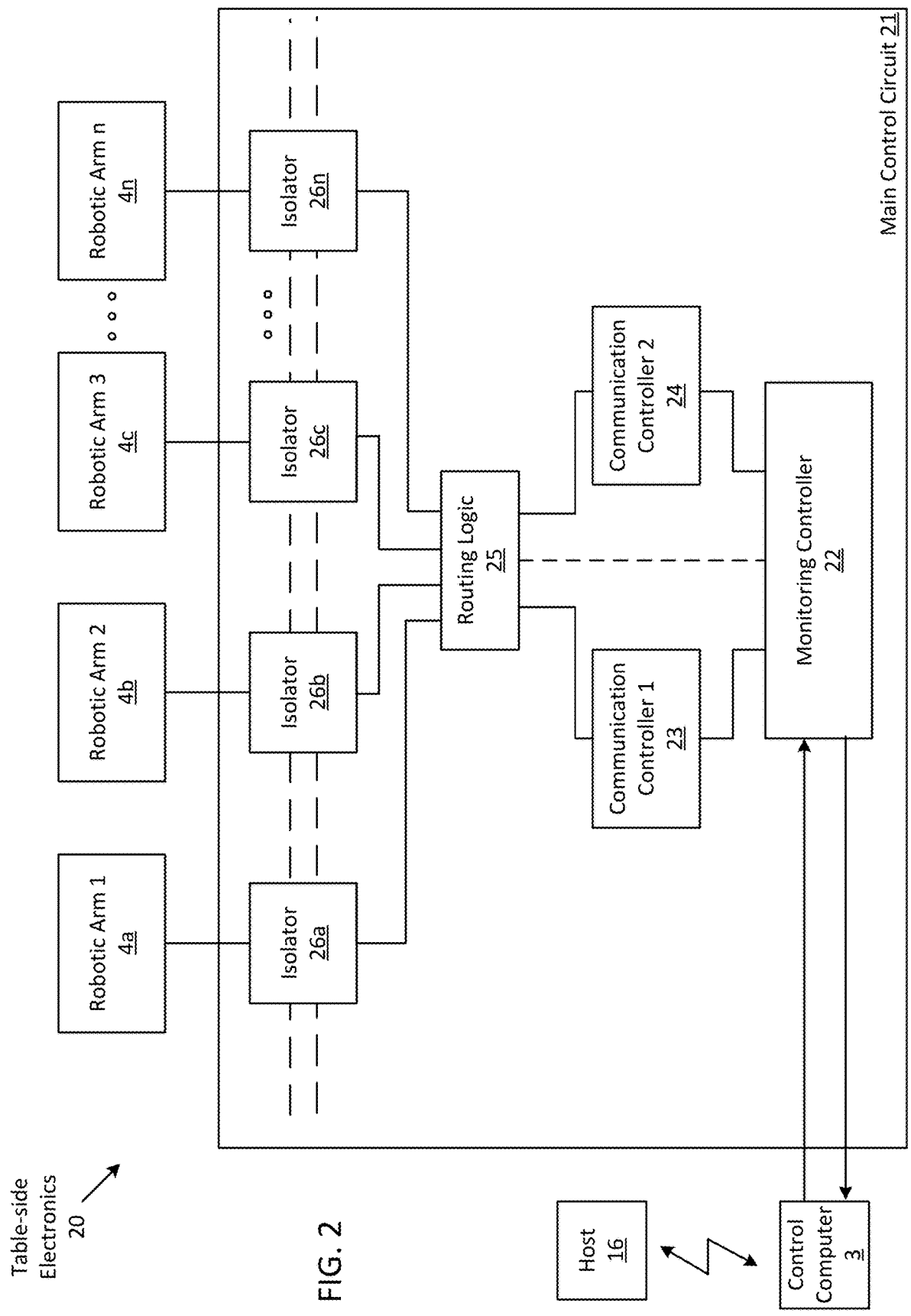
FIG. 2 shows redundant communication architecture of table-side electronics of a surgical robotic system that has at least two communication controllers according to one embodiment.

FIG. 2 shows a redundant communication architecture of table-side electronics of a surgical robotic system that has at least two communication controllers according to one embodiment. Specifically, this figure illustrates table-side electronics (or an electronic circuit) 20 that has the redundant communication architecture in order to ensure that the surgical robotic system 1 is fault-safe against one or more faults that may occur within the system. In particular, the electronics includes a main control circuit 21 that is arranged to communicate with the host 16 over a connection in order to exchange data (e.g., receiving robotic control commands, etc.) and with components of the robotic system (e.g., the arms 4a-4n), and that maintains communication between the host and the arms in case of a fault within the system. The main control circuit includes two separate communication controllers, communication controller 1 (first communication controller or first controller) 23 and communication controller 2 (second communication controller or second controller) 24, which both operate independently from one another. The electronics are redundant in that one of the controllers has a "master responsibility" of facilitating the communication between the host 16 and components within the system, such as one or more of the robotic arms 4a-4n, while the other controller is redundant (e.g., is not communicatively coupled to the robotic arms 4a-4n so as to instruct the arms to perform one or more operations). When a fault occurs, such as a failure of the controller with the master responsibility, the redundant controller is given the master responsibility of facilitating the communication thereby ensuring that communication between the host and the arms is not interrupted. As another example, the system may be fault-safe against multiple or double faults, which may occur within one or more of the components within the system 1. More details about the redundancy of the table-side electronics is described herein.

In one embodiment, the main control circuit 21 enables communication between one or more of the robotic arms 4a-4n and the host 16 (via the control computer 3). Specifically, the main control circuit is configured to establish communication, via a connection, with the host 16 via the control computer 3 in order to exchange data. In one embodiment, the connection may be a wired communication line (e.g., via a fiber optic cable or a coaxial cable) or a wireless link using any wireless protocol, such as BLUETOOTH protocol. In one embodiment, the main control circuit includes one or more electronic components, such as circuit boards that includes components integrated thereon as described herein that enable communication. For instance, the control circuit includes a monitoring controller 22, the first controller 23, the second controller 24, routing logic 25, and isolators 26a-26n, one isolator for each of the robotic arms 4a-4n. In one embodiment, at least some of the elements of the control circuit, such as the three controllers make up a redundant communication system of the main control circuit 21.

In one embodiment, the monitoring controller 22, the first controller 23, the second controller 24, and/or routing logic 25 may each be (or include) separate electronic devices that include one or more processors that are configured to perform one or more computational operations. For example, the first controller 23 and the second controller 24 may each be separate Systems on Modules (SOMs). In another embodiment, the first and second controllers may be the same electronic devices (e.g., each being the same SOM that includes similar components) that are configured to perform at least some of the same operations. More about the first and second controllers is described herein.

The communication controllers 23 and 24 are configured to route input data (e.g., robotic control commands) from the control computer 3 to particular arms 4a-4n, and route data (e.g., response signals) obtained from the arms as output data (e.g., feedback signals) back to the host. For example, the controller with the master responsibility may process and route robotic control commands that are received from the host, each including one or more instructions to drive at least one arm to perform a movement, to one or more robotic arms. In particular, the controller may packetize (or re-packetize) the robotic control commands as joint command signals, which are transmitted to the appropriate arms. In one embodiment, a joint command signal causes (e.g., an actuator or motor of the) particular robotic arm to perform a movement according to the instructions of the packetized robotic control command. The same controller may transmit the joint command signal to the particular robotic arm, via the routing logic 25. As described herein, the system may be redundant such that both controllers may perform similar operations to one another. For instance, both controllers may process the robotic control commands to produce the joint command signal. However, only the controller with the master responsibility is able to transmit the joint command signal. More about the communication controllers and the master responsibility are described herein.

The monitoring controller 22 is communicatively coupled (e.g., via the communication connection) with the host 16 via the control computer 3 in order to exchange data as described herein. The monitoring controller is also coupled to both communication controllers 23 and 24. The monitoring controller is configured to monitor the data being exchanged with the host 16, and data being produced by both communication controllers to determine whether the controller with the master responsibility should maintain the responsibility or whether the responsibility should be handed off to the other controller. For instance, upon detecting a fault (e.g., within the communication with the host), the monitoring controller may signal that the redundant controller is to have the master responsibility instead of the controller that currently has the responsibility. More about the operations of the monitoring controller is described herein.

The routing logic 25 are coupled between each of the isolators 26a-26n and both communication controllers 23 and 24, and is arranged to communicatively couple the communication controllers and monitoring controller with the robotic arms 4a-4n. In one embodiment, the routing logic is configured to route signals received from one or more of the robotic arms to at least one of the controllers. In another embodiment, the logic is configured to route signals received from only one of the communication controllers (e.g., the communication controller with the master responsibility as described herein) to one or more robotic arms. In one embodiment, the routing logic 25 may include ICs, such as transistors or switches) that select which communication controller can communicate with the arms 4a-4n, via corresponding isolators 26a-26n. The routing logic may also include one or more drivers that are arranged to transmit signals back to the communication controllers and/or to the monitoring controller. In one embodiment, the logic may include separate ICs for each of the robotic arms, such as having routing logic 25a coupled between isolator 26a and the communication controllers (and the monitoring controller). In one embodiment, the routing logic 25 is configured to switch communication between both communication controllers based on control signals obtained from the monitoring controller. More about the routing logic is described herein.

The isolators 26a-26n may be any type of digital isolator that is configured to electrically isolate the components of the main control circuit (e.g., the routing logic 25) from the components of the robotic arms (e.g., circuit boards and/or motors within the robotic arms). Thus, the isolators prevent any electrical noise from being transmitted between the main control circuit 21 and the robotic arms. In one embodiment, the isolators may be low-voltage differential signaling (LVDS) isolators. In another embodiment, at least some of the isolators may be opto-isolators that isolate the two components using light transmission.

Figure 3:
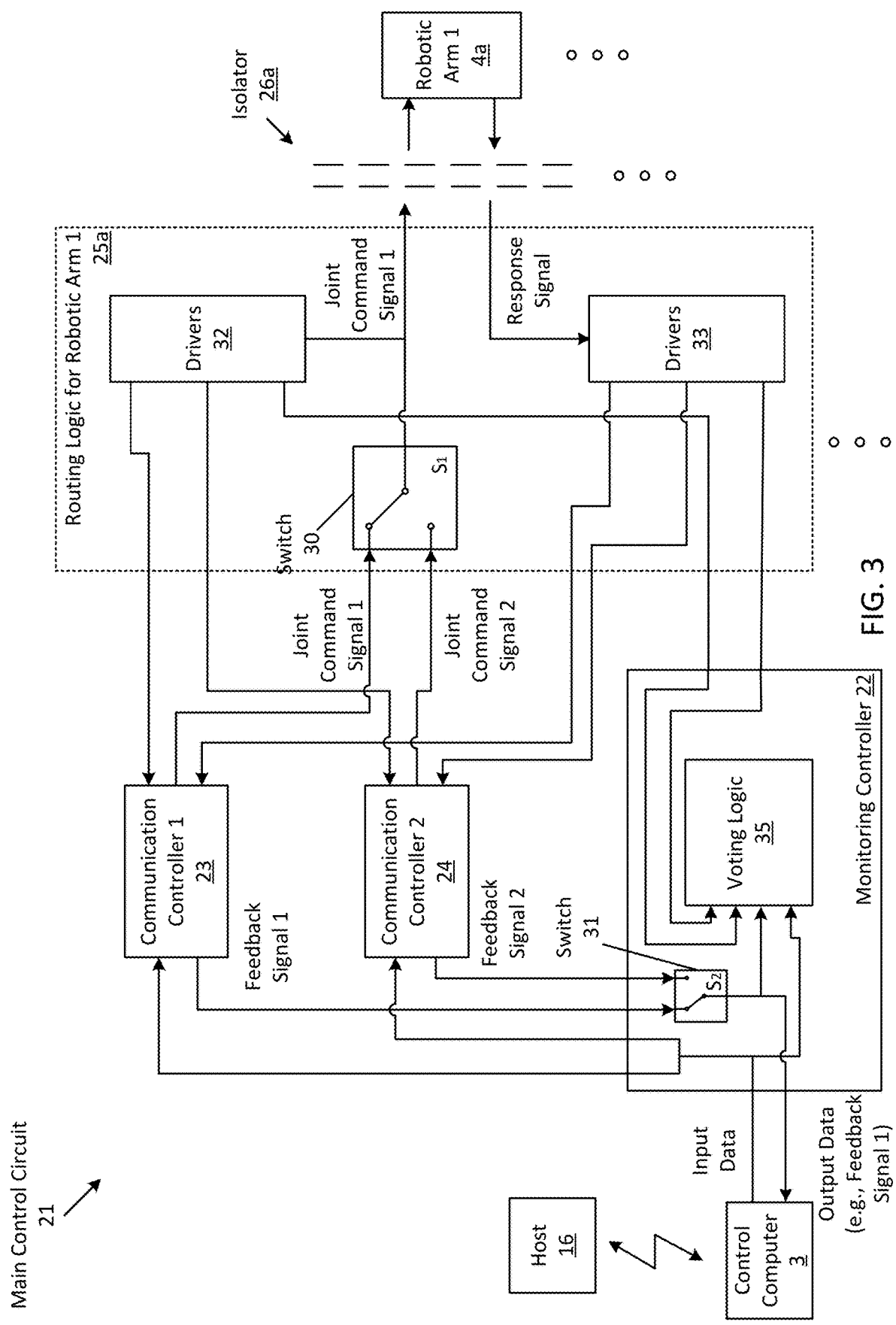
FIG. 3 illustrates a main control circuit of table-side electronics in which one of two communication controllers has a master responsibility according to one embodiment.

FIG. 3 illustrates a main control circuit of table-side electronics in which one of the two communication controllers has a master responsibility according to one embodiment. Specifically, this figure illustrates that the first communication controller 23 has the master responsibility for facilitating communication between the host 16 and at least one robotic arm (e.g., robotic arm 1 4a). For instance, the monitoring controller 22 obtains input data from the host 16 via the control computer 3. In one embodiment, the input data may be robotic control commands that are translated from user commands (or control signals) by the control computer 3. The monitoring controller relays the input data to both communication controllers 23 and 24. In one embodiment, the monitoring controller may only relay (or route) data to the communication controllers that relates to the operation or movement of the robotic arms, such as when the data includes robotic control commands.

The communication controllers 23 and 24 are both configured to receive the robotic control commands that include instructions to drive at least one robotic arm to perform a movement, and are configured to process the robotic control commands as joint command signals. For instance, the controllers may process the robotic control commands by packetizing the data based on a communication protocol with which the controllers communicate with the robotic arms. For example, the robotic control commands may be data produced using transportation protocols, such as Transmission Control Protocol and the Internet Protocol (TCP/IP). In one embodiment, the communication between one or more components within the table-side electronics may use a different communication protocol. Thus, both controllers produce separate joint command signals (e.g., communication controller 23 produces joint command signal 1 and communication controller 24 produces joint signal 2) and transmit the signals to the routing logic for robotic arm 1 25a. In one embodiment, only the controller with the master responsibility produces the joint command signal, which are packetized robotic control commands, as described herein.

The routing logic 25a includes a switch 30 ($S_1$) and several drivers 32 and 33. $S_1$ is configured to receive joint command signals from both of the communication controllers 23 and 24, but is only configured to allow one of the signals to be routed to the robotic arm 1 4a. Specifically, $S_1$ is configured to route the joint command signal 1 to the robotic arm 1 4a, via the isolator 26a. Thus, the communication controller 23 has the master responsibility since the switch enables the communication controller to communicate with the robotic arm 4a. As described herein, $S_1$ may be communicatively coupled to the monitoring controller and may be configured to route signals from the second communication controller in response to receiving a control signal from the monitoring controller. In other words, the position of $S_1$ indicates which communication controller has the master responsibility. More about controlling $S_1$ is described herein.

Along with routing the joint command signal 1 to the isolator 26a, the routing logic 25a is configured to route the joint command signal 1 to drivers 32 that route the joint command signal back to at least one of the first communication controller 23, the second communication controller 24, and the monitoring controller 22. In one embodiment, the drivers 32 may be driver circuits that include electrical components (e.g., one or more transistors) that are configured to receive the joint command signal that is being passed through by $S_1$ (in this case joint command signal 1) and transmit the signal to a respective controller. In another embodiment, the drivers 32 may include separate driver circuits for each controller to which the joint command signal is relayed. Thus, the drivers 32 may include at least three driver circuits.

In one embodiment, once the joint command signal, which is based on an instruction from the user or operator, is transmitted to the robotic arm 1 4a, via the isolator 26a, the robotic arm 1 may perform an operation. For example, the instruction may include a one-inch vertical movement of the arm 4a. The joint command signal may control a motor node of the robotic arm 1 to cause the motor to activate and to lift the arm vertically by one inch.

In one embodiment, the robotic arm 1 4a may be configured to transmit a response signal back to the host in order to provide confirmation of the movement. In one embodiment, the response signal may include other data or information, such as the current position of the robotic arm (with respect to the surgical table) or the overall status of the robotic arm. In another embodiment, the response signal may be based on the completion of (or inability to complete) a last instruction that is received by the robotic arm. In some embodiments, the response signal may be a signal that is transmitted periodically (e.g., every second). The response signal is transmitted by the robotic arm to the routing logic for the arm 25a, via the isolator 26a. Specifically, the response signal is received by the drivers 33, which then route the response signal to at least one of the first communication controller 23, the second communication controller 24, and the monitoring controller 22. In one embodiment, the drivers 33 may be similar to the drivers 32. For example, the drivers 33 may include separate driver circuits for each of the controllers to which the drivers 33 route data or signals. In particular, the drivers 33 may include three driver circuits, one for each of the first communication controller 23, the second communication controller 24, and the monitoring controller 22.

Both of the communication controllers receive, from the robotic arm 4a (via the routing logic 25a), the response signal. For instance, the response signal may include an indication of the movement performed by the arm in response to receiving the joint command signal 1. Once received, the controllers are configured to produce and transmit a feedback signal based on the indication in the response signal to the host 16. As illustrated, the first communication controller 23 produces feedback signal 1 and the second communication controller 24 produces feedback signal 2. As described herein, components within the system 1 may communicate according to a communication protocol, and thus the response signal may be in the communication protocol. When producing the feedback signals, however, the communication controllers may process the data according to the protocol (e.g., the transportation protocol) for which the input data was received in order to communicate the data back to the host. Thus, both controllers process the response signal by packetizing the response signal according to the transportation protocol to produce feedback signals 1 and 2, which are both received by the monitoring controller 22. Thus, the feedback signals are packetized version of the response signals according to the transportation protocol.

The monitoring controller 22 includes a switch ($S_2$) 31 and voting logic 35. $S_2$ is configured to receive data (e.g., feedback signals) from both of the communication controllers 23 and 24, and is configured to route feedback signals from the communication controller with the master responsibility (e.g., feedback signal 1) to the host 16 as output data. In this case, since the first communication controller 23 has the master responsibility, $S_2$ is positioned to allow only feedback signals from the first communication controller 23 to pass through.

The monitoring controller 22 is configured to determine whether a fault within the communication architecture is detected in order to determine whether the master responsibility should be handed off to another communication controller. Specifically, the voting logic 35 is configured to receive at least one of 1) input data from the control tower 3, 2) output data (e.g., feedback signal 1) from the $S_2$, 3) the response signal from drivers 33, and 4) the joint command signal that is routed to the robotic arm 4a by $S_1$, which is in this case joint command signal 1. The voting logic is configured to determine whether the communication controller that has the master responsibility (the first communication controller 23) should maintain the responsibility or should give the responsibility to the other communication controller.

To determine this, the (voting logic of the) monitoring controller determines whether a fault is detected within the first communication controller 23 based on the signals being produced by the controller 23. For example, the voting logic determines whether feedback signals are properly produced by the first communication controller 23. For instance, the voting logic 35 produces an expected feedback signal based on the response signal that is routed by the drivers 33 to each of the three controllers. The voting logic 35 may perform the same operations as performed by the communication controllers (e.g., processing the response signal to packetize the response signal according to a transportation protocol to produce the expected feedback signal). The voting logic compares the expected feedback signal produced by the voting logic with the feedback signal 1 produced by the first communication controller that is received from $S_2$. If the signals are the same, this may mean that the first communication controller is properly producing the feedback signals, and therefore there is no fault detected within the controller. In one embodiment, a fault is not detected when the feedback signals are similar up to a threshold difference (e.g., 10%). If, however, the signals are dissimilar (e.g., exceeding the threshold difference), the voting logic may determine that a fault is detected within the first communication controller.

As another example, the (voting logic 35 of the) monitoring controller 22 may determine that a fault within the first communication controller 23 is detected based on signals produced by the controller that are transmitted to the robotic arms (e.g., arm 4a). For instance, the voting logic may use the input data (e.g., a robotic control command) to produce an expected joint command based on an instruction, such as an arm movement, within the robotic control command. Specifically, the voting logic 35 may packetize the robotic control command based on the communication protocol to produce the expected joint command. The voting logic compares the expected joint command signal with the joint command signal 1 produced by the first communication controller 23 that is routed by the drivers 32. If the signals are the same (or within a threshold difference), the voting logic may not detect a fault. If, however, the signals are different, the voting logic may detect a fault with the first communication controller.

In one embodiment, routing logic 25 of at least some of the other robotic arms 4b-4n may include at least some of the components described herein for routing logic 25a of robotic arm 4a. Thus, the operations described herein may also be performed for any of the routing logic and a respective robotic arm.

Figure 4:
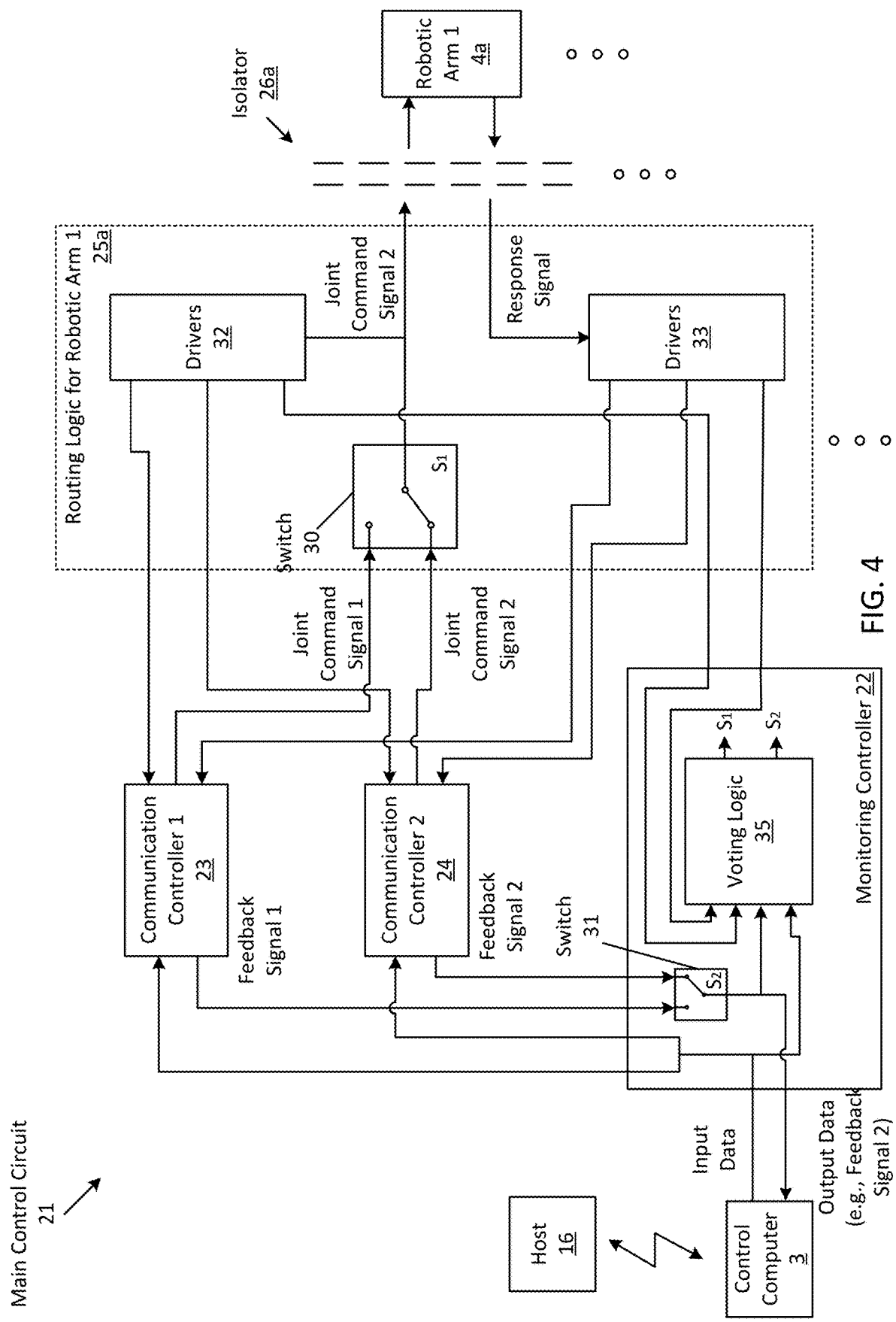
FIG. 4 illustrates that the master responsibility of a communication controller has been given to another communication controller in response to detecting a fault in the table-side electronics according to one embodiment.

When a fault is not detected, the monitoring controller maintains the configuration with the first communication controller maintaining the master responsibility. If, however, a fault is detected, the monitoring controller is configured to signal that the second communication controller 24 is to have the master responsibility instead of the first communication controller. FIG. 4 illustrates that the master responsibility of a communication controller has been given (or handed off) to another communication controller in response to detecting a fault in the table-side electronics according to one embodiment. Specifically, the (voting logic 35 of the) monitoring controller 22 signals that the second communication controller 24 is to have the master responsibility instead of the first communication controller 23. For instance, to signal the change, the monitoring controller configures the routing logic to prevent the first communication controller from transmitting future joint command signals to the robotic arm and allow the second communication controller to transmit future joint command signals processed from future robotic control commands to the robotic arm. The monitoring signal may also signal the change by preventing the first communication controller from transmitting future feedback signals to the host and allowing the second communication controller to process and transmit future response signals as future feedback signals to the host. In particular, voting logic 35 transmits controls signals to both switches $S_1$ and $S_2$ to cause both switches to change positions. The control signal to $S_1$ causes the switch to allow joint command signals 2 produced by the second communication controller 24 to pass through; and the control signal to $S_2$ causes the switch to allow feedback signals 2 produced by the second communication controller 24 to pass through. In one embodiment, the first communication controller 23 may remain operational (e.g., producing joint command signals and feedback signals), even though a fault has been detected. In another embodiment, the monitoring controller may signal the first communication controller to switch off.

In one embodiment, $S_1$ and $S_2$ may be any type of electronic switches that have one or more input terminals and one or more output terminals. For instance, the switches may include switching components (e.g., transistors), that may be controlled via an electrical signal.

In some embodiments, the (e.g., monitoring controller 22 of the) main control circuit 21 may output an alert in response to detecting a fault. For example, the monitoring controller may transmit, as output data, an alert signal to the host 16 to alert the operator 9 of the detected fault. In one embodiment, the alert signal may be an audio signal that is outputted through one or more speakers. In another embodiment, the alert signal is a visual message that is displayed on the display screen 15. In one embodiment, the alert may be outputted by the table-side electronics 20 (e.g., by speakers of the electronics 20) in order to alert users within the operating room.

In one embodiment, the main control circuit 21 may be communicatively coupled to the surgical table 5 in a similar fashion. Specifically, the surgical table may include one or more driver mechanisms (e.g., actuators and/or motors) in order to manipulate or adjust the position of the table. For example, the table may include actuators coupled to a table top of the table in order to allow the table top to tilt upward. Thus, one or more components of the surgical table may be communicatively coupled with at least one of the communication controllers 23 and 24. For instance, both communication controllers may be communicatively coupled to the surgical table via routing logic (e.g., particular logic for each component of the table) that is controlled by the monitoring controller 22 as described herein. The communication controller with the master responsibility may exchange data with the surgical table (e.g., joint command signals and response signals) in a similar fashion as the robotic arms 4a-4n.

Figure 5:
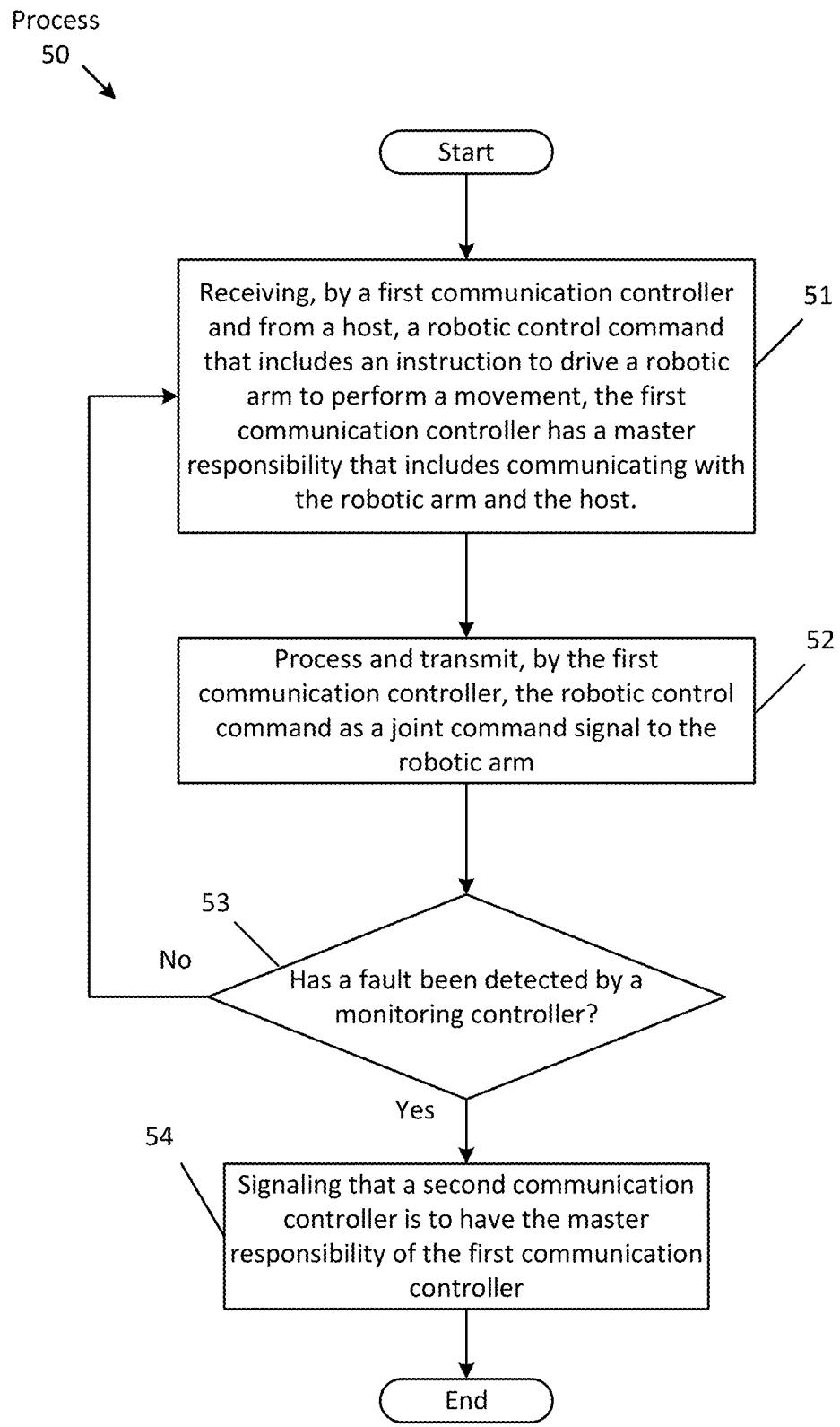
FIG. 5 is a flowchart of one embodiment of a process to hand off the master responsibility from one communication controller to another in response to detecting a fault according to one embodiment.

FIG. 5 is a flowchart of one embodiment of a process 50 to hand off the master responsibility from one communication controller to another in response to detecting a fault according to one embodiment. In one embodiment, the process 50 may be performed by the main control circuit 21 of the table-side electronics 20. Specifically, at least a portion of the process may be performed by any of the components (e.g., the first communication controller 23, the second communication controller 24, the monitoring controller 22, and the routing logic 25) of the main control circuit. The process 50 begins by receiving, at the first communication controller 23 and from the host 16, a robotic control command that includes an instruction to drive a robotic arm (e.g., arm 4a) to perform a movement, where the first communication controller has a master responsibility that includes communicating with the robotic arm and the host (at block 51). The process 50 processes and transmits, by the first communication controller, the robotic control command as a joint command signal to the robotic arm (at block 52). The process 50 determines whether a fault has been detected by the monitoring controller (at decision block 53). If not, the process 50 returns to block 51. If, however, a fault has been detected (e.g., by comparing an expected joint command signal with the joint command signal produced by the first communication controller), the process 50 signals that the second communication controller is to have the master responsibility of the first communication controller (at block 54).

Some embodiments perform variations of the process 50. For example, the specific operations of the process may not be performed in the exact order shown and described. The specific operations may not be performed in one continuous series of operations and different specific operations may be performed in different embodiments.

Figure 6:
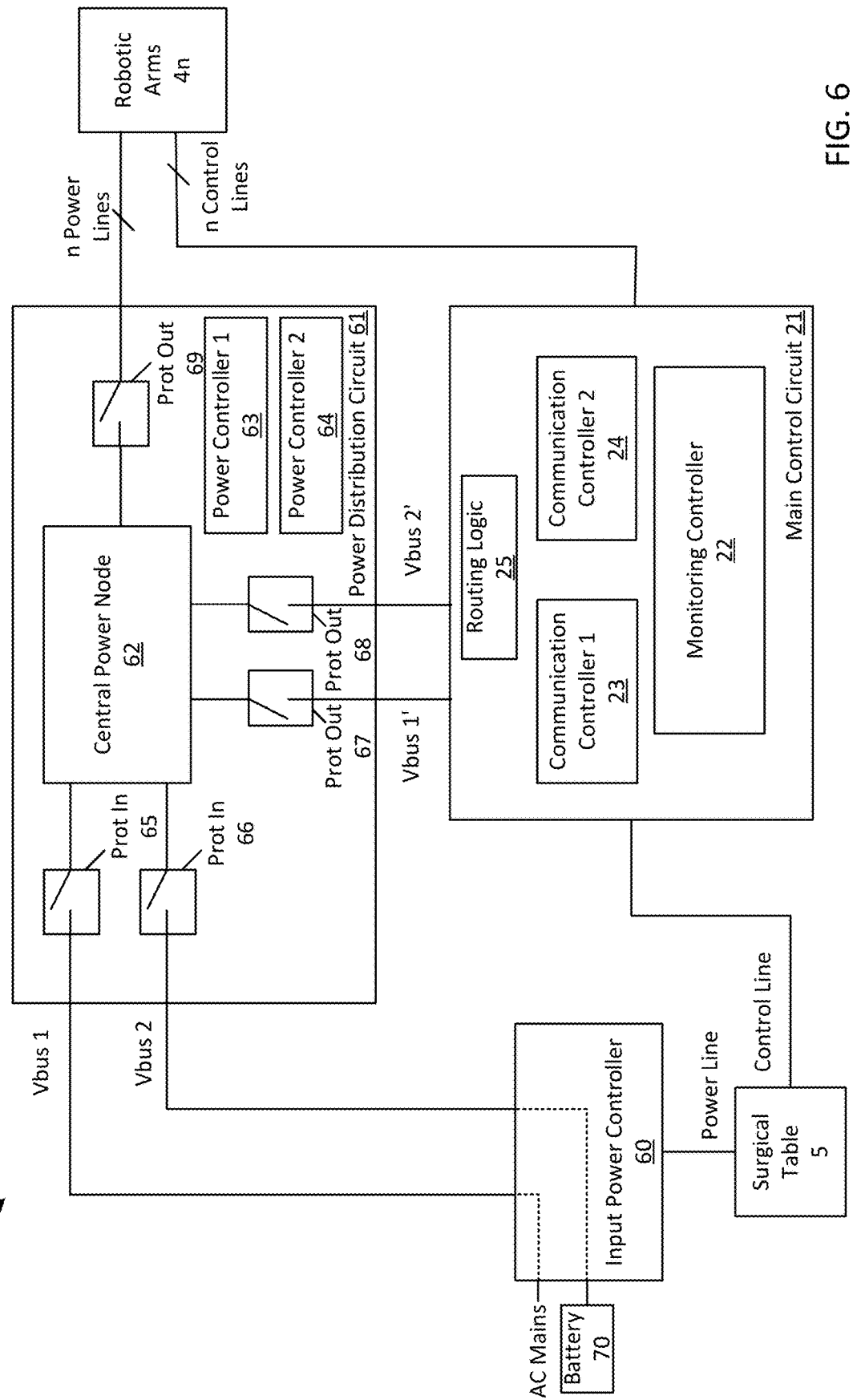
FIG. 6 shows redundant power architecture of table-side electronics of a surgical robotic system according to one embodiment.

FIG. 6 shows redundant power architecture of table-side electronics of a surgical robotic system according to one embodiment. Specifically, this figure illustrates the table-side electronics 20 that has the redundant power architecture in order to ensure that the surgical robotic system 1 is fault-safe against one or more faults that may occur within the system, such as short circuits. The electronics includes an input power controller 60, a power distribution circuit 61, and the main control circuit 21. The electronics also includes several busses, power lines, and control lines. Specifically, the table-side electronics 20 includes a first set of voltage busses, Vbus 1 and Vbus 2 that electrically couple the input power controller to the power distribution circuit, and include a second set of voltage busses, Vbus 1' and Vbus 2' that electrically couple the power distribution circuit to the main control circuit. Also, several power lines and control lines couple the robotic arms 4a-4n to the power distribution circuit and the main control circuit. For instance, each robotic arm may include at least one power line that electrically couples the arm to the power distribution circuit 61 (e.g., provides input power from the power distribution circuit 61) and at least one control line that communicatively couples the arm to the (routing logic 25 of the) main control circuit (e.g., in order to exchange data, such as joint command signals and response signals). Specifically, electronics (e.g., processors, actuators, motors, etc.) of the arms are electrically and communicatively coupled via the power and control lines, respectively. Also, the surgical table 5 is electrically coupled to the input power controller 60 via at least one power line (e.g., to provide input power) and the table is communicatively coupled to the main control circuit via at least one control line (e.g., in order to exchange data, such as joint command signals and response signals).

As illustrated herein, the components of the table-side electronics 20 may be coupled to one another. In one embodiment, the components are coupled together via lines, which may be wires that directly connect the components together. In another embodiment, the lines may be signal traces. In some embodiments, at least some of the components may be wirelessly connected (e.g., via BLUETOOTH protocol).

The table-side electronics 20 is configured to draw power from at least one of two input power sources: an Alternating Current (AC) mains power supply (AC mains) and a battery 70. In one embodiment, the battery may be any type of battery such as a lithium ion battery or lithium iron phosphate battery. In another embodiment, the battery may be housed in the surgical table 5, or the battery may be stored external to the surgical table 5 (e.g., as part of an Uninterruptible Power Supply (UPS) battery pack).

The input power controller 60 is configured to manage input power from at least one of the AC mains and the battery 70, and is configured to provide redundant input power to the rest of the table-side electronics 20 via the two separate busses, Vbus 1 and Vbus 2. Specifically, the input power controller 60 provides input power to the power distribution circuit 61 via (at least) one of Vbus 1 and Vbus 2. In one embodiment, the table-side electronics may include an AC/DC converter that is configured to receive AC power from the AC mains and convert the AC power into Direct Current (DC), which is then received by the input power controller. In one embodiment, the input power controller may provide AC mains power via Vbus 1, and provide redundant battery power from battery 70 via Vbus 2 when needed (e.g., when AC mains is down due to a power outage). Thus, the busses may be dedicated busses to their respective input power sources. For instance, as described herein, each of the busses may couple to the (central power node 62 of the) power distribution circuit 61 via a circuit breaker "Prot In". Thus, while Vbus 1 provides power, Prot In 65 may be closed and Prot In 66 may be opened, such that Vbus 1 is only supplying power. In another embodiment, the busses are not dedicated to the sources, such that input power from either source may be provided via either bus. In some embodiments, the input power controller provides input power via Vbus 1 and Vbus 2 simultaneously. For instance, the input power provided via Vbus 1 may be drawn from the AC mains, while input power provided via Vbus 2 may be drawn from the battery 70.

In one embodiment, the input power controller 60 is configured to switch from which input power source the input power is drawn in response to detecting a fault. Specifically, the input power controller 60 may be configured to detect a fault within the controller and/or within the busses Vbus 1 and Vbus 2. For instance, the input power controller 60 may provide input power via Vbus 2 that is drawn from the battery 70 while power drawn from the AC mains charges the battery, as described herein. The input power controller may measure the current flowing through Vbus 2 and may determine whether the current exceeds a threshold which is indicative of a short circuit. When the input power controller detects the short circuit, the controller may cease providing input power via Vbus 2 (e.g., by causing Prot In 66 to open) and begin providing input power (e.g., from the AC mains) via Vbus 1 (e.g., by causing Prot In 65 to close). In one embodiment, the input power controller 60 may include one or more circuit breakers, which may be opened or closed based on whether a fault is detected. As another example, when input power is being provided by both input power sources simultaneously on their respective busses, the input power controller may cease providing input power from one of the sources in response to detecting a fault while input power is still being provided by the other source. Thus, table-side electronics may continue to provide power even in cases in which a fault is detected.

As described herein, the input power controller 60 is electrically coupled to the surgical table (e.g., electrical components of the surgical table, such as actuators, motors, circuit components, etc.) via a power line. In one embodiment, the input power controller may provide the same input power to the surgical table 5 via the power line as the input power being provided to the rest of the electronics 20. For instance, when the input power controller provides battery power from battery 70 via Vbus 2 to the power distribution circuit 61, the controller 60 may provide battery power to the surgical table 5 via the power line.

The power distribution circuit 61 includes a redundant power architecture that manages and distributes input power that is received from at least one of the Vbus 1 and Vbus 2 to the robotic arms 4n and the main control circuit 21. In one embodiment, the power distribution circuit may include one or more electronic components or devices (e.g., circuit boards) that enable the distribution of the input power. For instance, the circuit includes several circuit breakers 65-69, a central power node 62, a first power controller 63 and a second power controller 64.

The central power node 62 is electrically coupled to 1) the input power controller 60 via Vbus 1 and Vbus 2, 2) the main control circuit 21 via Vbus 1' and Vbus 2', and 3) to each of the robotic arms 4a-4n via at least one power line. In one embodiment, the central power node is an electronic component that is configured to distribute power between the busses and/or the power lines. For instance, the node may include at least one conductor of electricity, such as copper in order to distribute power from the input power controller to the main control circuit and/or the robotic arms.

As illustrated, Vbus 1 electrically couples the AC mains to the node 62 and Vbus 2 electrically couples the battery 70 to the node. The node includes several circuit breakers, input circuit breakers (Prot In) that protect the node 62 along paths through which input power is received and output circuit breakers (Prot Out) that protect components along paths through which the node provides the input power. Specifically, Prot In 65 is coupled between Vbus 1 and the node 62, Prot In 66 is coupled between Vbus 2 and the node 62, Prot Out 67 is coupled between Vbus 1' and the node 62, and Prot Out 68 is coupled between Vbus 2' and the node 62. In addition, the power distribution circuit includes a Prot Out 69 that couples each robotic arm to the node 62, via a respective power line. In one embodiment, each of these circuit breakers may include a unidirectional circuit breaker and at least one diode. The input circuit breakers may act to isolate the node from the busses in case one of them should short out or draw excessive backflow current, but does allow non-limited current to flow from the busses and into the node. Thus, each of the input circuit breakers protect the node from an excessive amount of current (e.g., above a first threshold) flowing out of the node via a respective bus. Thus, the input circuit breakers limit an output current flow (first output current flow) from the node into the bus. The output circuit breakers are arranged to limit (a second) output current (e.g., current flowing from the breakers and into each arm and/or the main control circuit) but allow non-limited current flow back into the node (e.g., during regeneration current events).

In one embodiment, each of the circuit breakers may automatically switch (e.g., Prot Out 67 may trip creating an open circuit in response to sensing high current, above a threshold, along Vbus 1'), or may be controlled to switch under certain conditions. Specifically, both of the first and second power controllers 63 and 64 are communicatively coupled to each of the circuit breakers, and are configured to control each of the circuit breakers independently. The circuit breakers may need to be opened under certain conditions. For example, when the system is deactivated, the controllers may cause each (or at least some) of the circuit breakers to open in order to deactivate the system. As another example and as previously described, the controllers may control the circuit breakers in order to only allow one of Vbus 1 and Vbus 2 to provide power. In another embodiment, the power controllers may obtain sensor data that is used to determine which circuit breakers to open. Thus, the decision to open/close a particular circuit may be made only by the power controllers 63 and/or 64. In one embodiment, each of the power controllers may obtain commands from at least one of the communication controllers 23 and/or 24 to open/close specific circuit breakers. More about how the circuit breakers are controlled is described herein.

Figure 7:
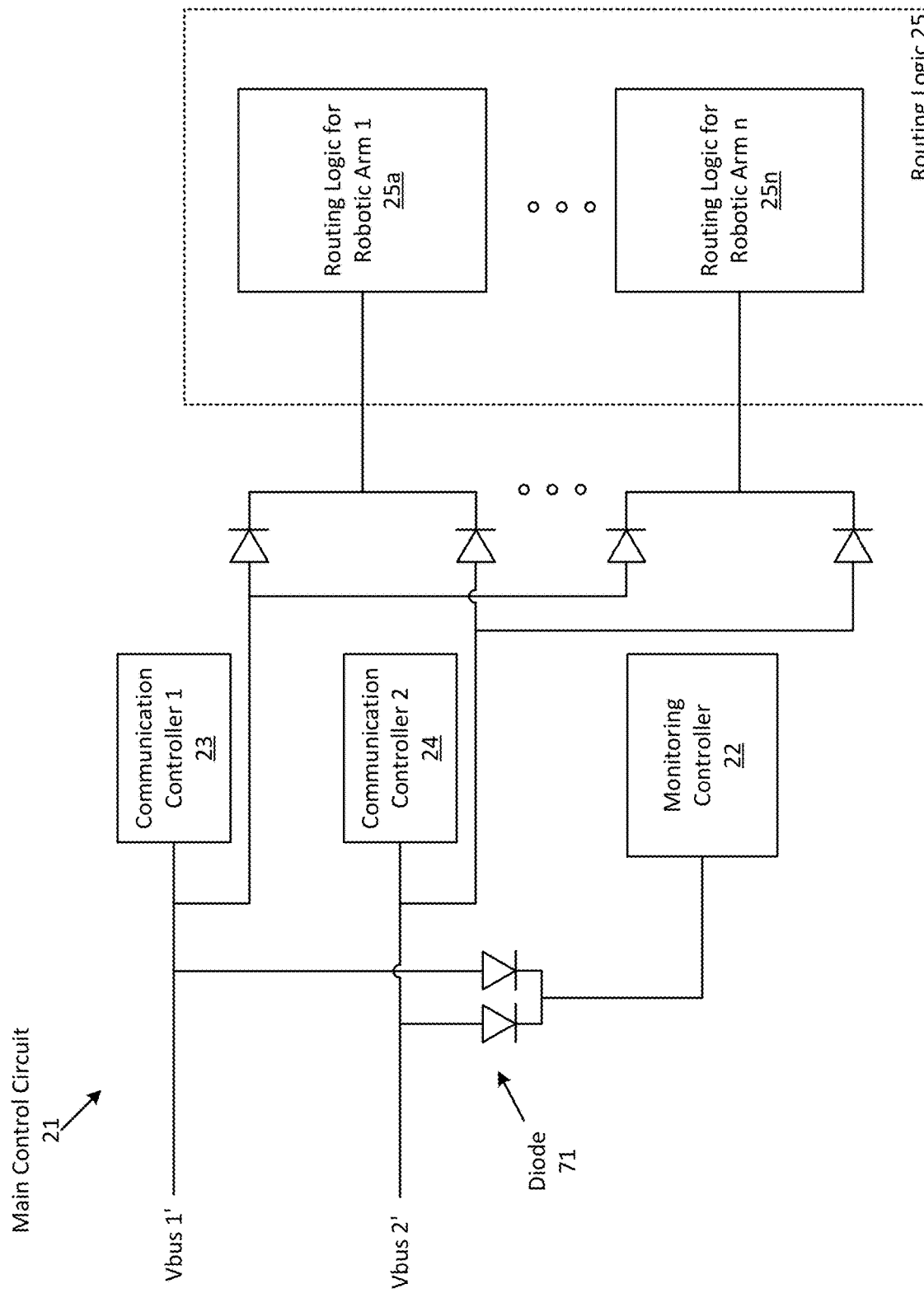
FIG. 7 shows redundant power architecture of a main control circuit of table-side electronics of a surgical robotic system according to one embodiment.

FIG. 7 shows redundant power architecture of a main control circuit of table-side electronics of a surgical robotic system according to one embodiment. Specifically, this figure shows how the main control circuit 21 is powered by the power distribution circuit 61 via the second set of busses, Vbus 1' and Vbus 2'. As shown, the first communication controller 23 is powered by Vbus 1', the second communication controller 24 is powered by Vbus 2', and the monitoring controller 22 and routing logic for each respective robotic arm 25a-25n are powered based on a combination of Vbus 1' and Vbus 2'. Coupled between each of the busses and the monitoring controller 22, and routing logic of each robotic arm is a diode 71 that allows current to only flow from the busses to the components. In one embodiment, rather than (or in addition to) diodes the main control circuit 21 may include current limited devices, so that an output short will not short out both input ports of the of the busses. As a result, when one of the output circuit breakers (e.g., Prot Out 67) is tripped (e.g., due to a fault) Vbus 1' will cease providing power, however, the main control circuit 21 will continue to be supplied power via Vbus 2' so long as Prot Out 68 remains closed. Specifically, when a single fault occurs along a particular bus, only the communication controller that draws power from the particular bus may be affected (e.g., deactivated), while the other components continue to draw power from the other bus. Thus, the main control circuit 21 will continue to operate even in a situation in which a fault occurs.

In one embodiment, the communication controllers will switch master responsibility in response to a fault occurring within the power architecture. For example, the first communication controller receives power via Vbus 1' and the second communication controller receives power from Vbus 2'. When a fault occurs, the power distribution circuit trips Prot Out 67. In one embodiment, the monitoring controller 22 may detect the fault as determining that the first communication controller is not receiving power from Vbus 1'. In response, the monitoring controller 22 may signal that the second communication controller 24 is to take master responsibility as described herein.

In one embodiment, the main control circuit 21 may include additional electronic components to regulate power that is being supplied by the power distribution circuit 61. For example, each of the controllers 22-24 and routing logic 25a-25n may include power supplies that regulate the power being distributed to the respective components.

Figure 8:
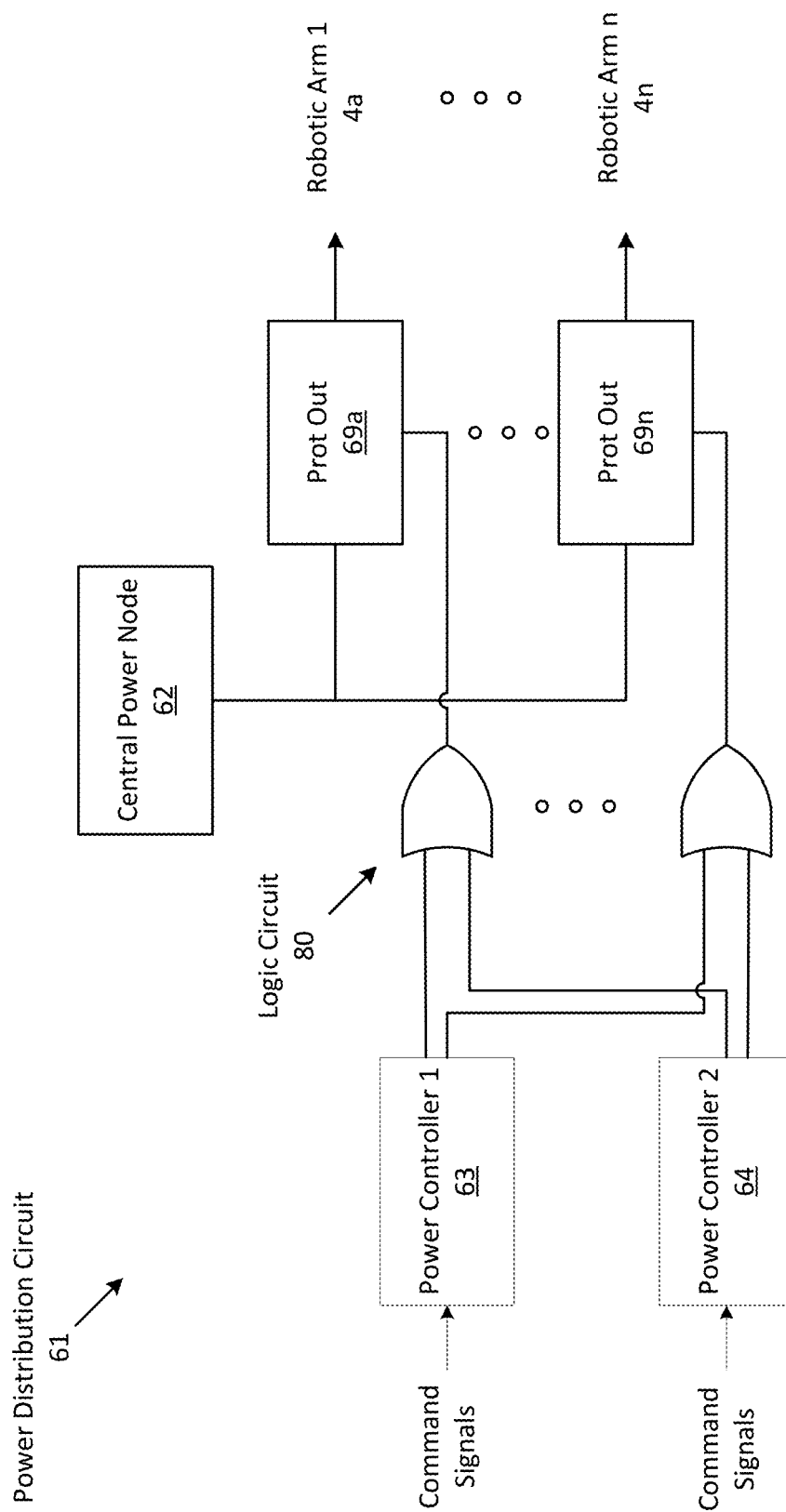
FIG. 8 illustrates a power distribution circuit of table-side electronics that has at least two power controllers according to one embodiment.

FIG. 8 illustrates a power distribution circuit of table-side electronics that has at least two power controllers according to one embodiment. As described herein, the circuit breakers (e.g., 65-69) may be independently controlled by both power controllers 63 and 64. Specifically, in order to prevent a fault within one of the controllers causing one or more circuit breakers to inadvertently open, causing a power outage over a respective bus and/or power line, both controllers must agree to open a circuit breaker. Thus, the circuit breakers may only open in response to both power controllers transmitting control signals that indicate instructions to open the breakers. As illustrated in this figure, output of each of the power controllers enters a logic circuit 80 that includes an OR logical element for each circuit breaker 69a-69n for a corresponding robotic arm 4a-4n. As an example, if the power controller 63 is faulty and transmits a control signal to the logic circuit to deactivate (or open) Prot Out 69a (e.g., a low control signal) in order to power down the robotic arm 4a, Prot Out 69a will remain closed so long as the second power controller 64 does not transmit the same control signal. Specifically, Prot Out will remain closed so long as the power controller 64 produces a high control signal. Thus, the remainder of the circuit breakers (e.g., the output circuit breakers) will remain closed in response to at least one of the power controllers transmitting a control signal (high signal) that includes instructions to close the remainder of the breakers. In one embodiment, so long as both power controllers 63 and 64 do not transmit control signals (e.g., both producing a low control signal), the circuit breakers will remain closed. In one embodiment, although not illustrated, each of the power controllers 63 and 64 may be coupled to the input circuit breakers, via the logic circuit.

In one embodiment, each of the first and second power controllers may receive command signals that instruct the controllers to open/close particular circuit breakers. In one embodiment, the power controllers may receive command signals from the (e.g., communication controller with the master responsibility and/or monitoring controller 22 of the) main control circuit 21 and/or receive command signals from the input power controller 60. For example, the input power controller 60 may transmit a command signal to power down one of the robotic arms. So long as both power controllers 63 and 64 receive the same command signal, the output circuit breaker to the arm will be opened. Thus, along with protecting the components from faults within one of the power controllers, the logic circuit 80 also provides protection from faulting command signals, which may cause one of the power controllers to provide an erroneous (or incorrect) control signal.

As described herein, the surgical robotic system 1 may allow a user (e.g., a medical professional, such as a nurse or doctor) within an operating room to adjust a position of at least one of the robotic arms 4a-4n in cases in which communication with the host 16 has failed or has been terminated. For example, while a communication connection (or link) is established (e.g., a wired or wireless connection), the system may operate in a teleoperation mode in which the components of the system (e.g., the robotic arms 4a-4n and the surgical table 5) may only be controlled by the operator, via the host 16 and control computer 3. For example, the system may only enable the operator to control the robotic arms in order to prevent the arms from receiving contrasting commands from different sources. If, however, communication with the host is terminated or lost, the surgical robotic system 1 may become inactive (e.g., pausing the position of the robotic arms in order to prevent the arms from collapsing on the patient). In order to prevent caging the patient between the surgical table and the robotic arms, the present disclosure allows the system to enter a second mode or a local mode which allows the user to move the robotic arms in response to a user-actuated switch being actuated by the user. Thus, the present disclosure allows the user to uncage the patient in times in which communication with the host has been lost.

Figure 9:
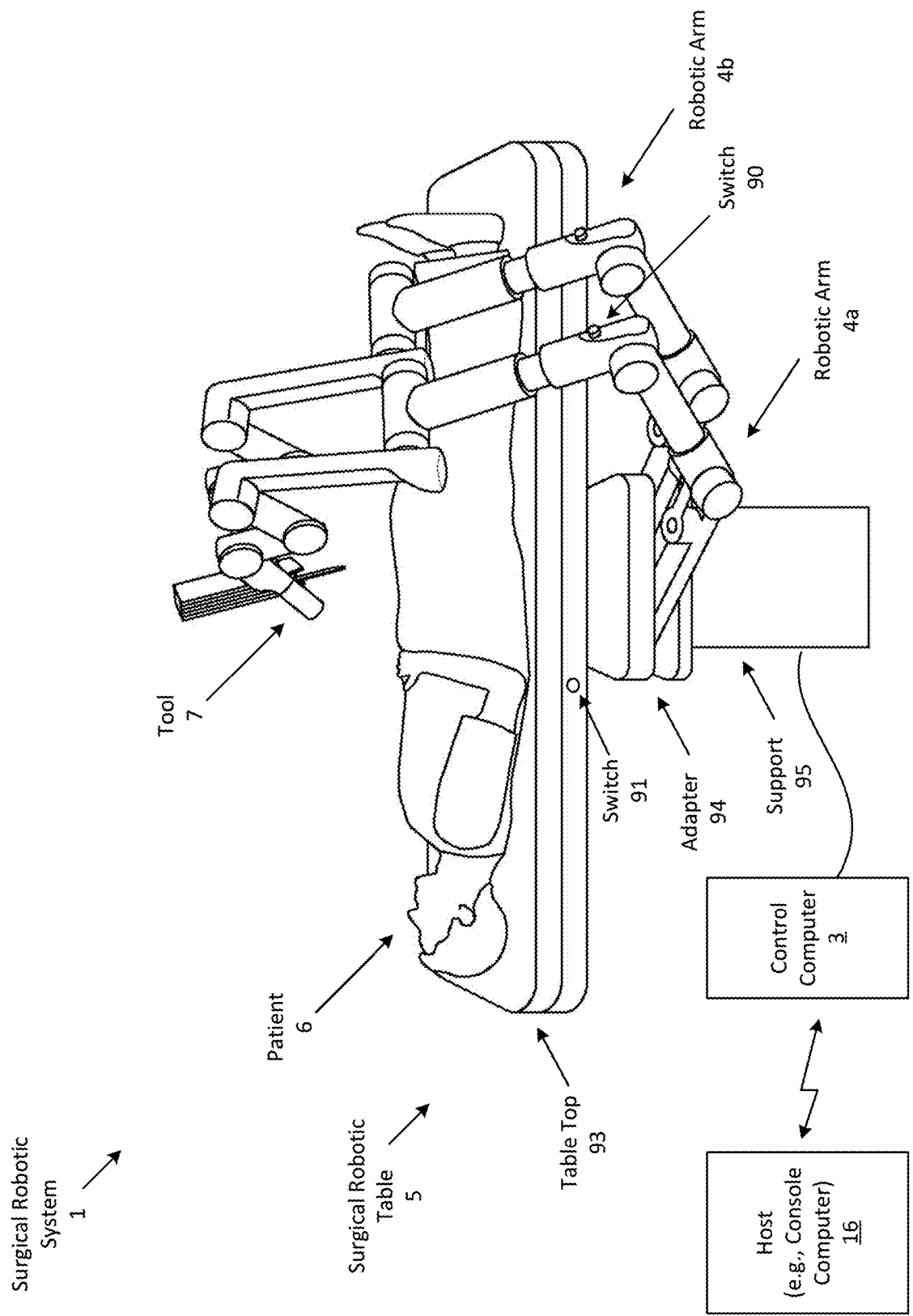
FIG. 9 shows a pictorial view of an example of a surgical robotic system with components that have user-actuated switches according to one embodiment.

FIG. 9 shows a pictorial view of an example of a surgical robotic system with components that have user-actuated switches according to one embodiment. Specifically, this figure shows the surgical robotic system 1 that includes the surgical robotic table 5, the control tower 3, and the host (e.g., console computer) 16. In one embodiment, the system 1 may include additional components as described in FIG. 1.

As illustrated, the surgical robotic table includes a table top 93, an adaptor 94, and a support 95. The table top has an upper surface on which the patient 6 is disposed during a surgical procedure, as shown. The table top is disposed on the adapter to which the robotic arms 4a and 4b are (pivotably) coupled. The adaptor is disposed on the support, which can be, for example, a pedestal, that has a suitable height above the floor. In one embodiment, the table may also include more or fewer components. For example, the table may include a base (not shown) on which the support is disposed on. As another example, the table may not include an adaptor, which as a result the robotic arms may couple to the tabletop and/or the support. In one embodiment, the surgical robotic table may include more or less robotic arms, such as at least four robotic arms (e.g., 4a-4d). For instance, two of the robotic arms may be on a first side of the table, while the other two robotic arms may be on a second side of the table that is opposite of the first side. As another example, all of the robotic arms may be positioned on one side of the table in order to allow users to gain access to the patient on the other side of the table.

Each of the robotic arms may include one or more links (or members) and one or more joints for actuating the links relative to one another and/or relative to the surgical robotic table 5. The joints may include various types, such as a pitch joint or a roll joint, which may substantially constrain the movement of the adjacent links around certain axes relative to others. In one embodiment, the arms may include at least one telescopic member that is configured to expand and contract relative to joints at either end of the member in order to vary its length. Each of the joints and telescopic members may include at least one driving mechanism, such as an actuator or motor that is configured to adjust the joint's (or telescopic member's) position according to a joint command signal that is received from the (e.g., communication controller with the master responsibility of the) table-side electronics as described herein. Each arm also includes a surgical tool 7 that is configured to removably couple to a distal end of the robotic arm. Thus, the joints of the robotic arms may be actuated to position and orientate the arms' tools to enable an operator of the surgical robotic system 1 to perform robotic surgeries.

Both of the arms also include a user-actuated switch 90 that is configured to enable a respective robotic arm to be moved by a user when actuated. In one embodiment, at least some of the arms may include one or more switches. When the switch is actuated or depressed by a user, a control signal is transmitted to the table-side electronics 20 (e.g., the communication controller with the master responsibility, such as the first communication controller 23) that indicates a user request to manually move the robotic arm. In response, the communication controller may enable at least one of the joints of the robotic arm to be (manually) moved by the user. For example, the communication controller may produce and transmit joint command signals based on user commands that are received by the user who is attempting to move the robotic arm. In one embodiment, user commands may be based on pulling/pushing force that is applied by the user upon the robotic arm. For instance, the robotic arm may include one or more force sensors (e.g., compression force sensors, tensile force sensors, etc.) that are configured to sense pushing and/or pulling force that is applied by an external object (e.g., a user's hand). These sensors transmit an electronic signal that includes sensor data, which indicates the amount of force and the direction at which the force is being applied, to the communication controller that then determines which joints of the robotic arm should be moved based on the data. The communication controller then transmits joint command signals to the joints in order to move the (joints of the) robotic arm based on the applied force. For instance, the joint command signals cause driving mechanisms within the joints of the robotic arm to assist movement of the robotic arm in a direction indicated by the signal. In one embodiment, the assisted movement may be based on the amount of force being applied to the robotic arm. For example, the driving mechanism may cause the robotic arm to move slowly in response to the applied force by the user being low (or below a threshold). Once the force is no longer applied (e.g., the user has stopped pushing or pulling on the robotic arm), the communication controller will cease transmitting the joint command signals. In another embodiment, the switch may include one or more controls (e.g., a joystick) that enable a user to direct the arm which way to move. In some embodiments, the switch may not be physically coupled to the robotic arm, but instead may be communicatively coupled (e.g., wired or wireless) with a separate electronic device (e.g., a computer tablet) that is configured to receive user input that indicates how to move the robotic arm.

This figure also illustrates that the surgical robotic table 5 includes a table user-actuated switch 91 that when actuated by the user enables the surgical table to be adjusted by the user. Similar to the robotic arms, the table 5 may include actuators or motors that are configured to move at least a portion of the table. For example, the table top may be arranged to couple to the adaptor at a joint that includes an actuator, and may be arranged to pivot about that joint (e.g., the table top may be pivotably coupled to the adaptor at the joint). Once the switch 91 is depressed, a user may push against one side of the table top 93 to cause the table top to rotate about an axis that runs vertically through the table. As another example, with the switch 91 depressed a user may tilt the table top with respect to the adaptor.

In one embodiment, the movement of the robotic arms and/or robotic table may only occur while the user is actuating respective switches. For example, a user may only move the robotic arm 4a, while switch 90 is being depressed. Once the switch is no longer depressed, the robotic arm may no longer respond to force that is applied to the arm. In another embodiment, the table-side electronics of the system may allow movement for a period of time (e.g., thirty seconds) after a switch is actuated.

Figure 10:
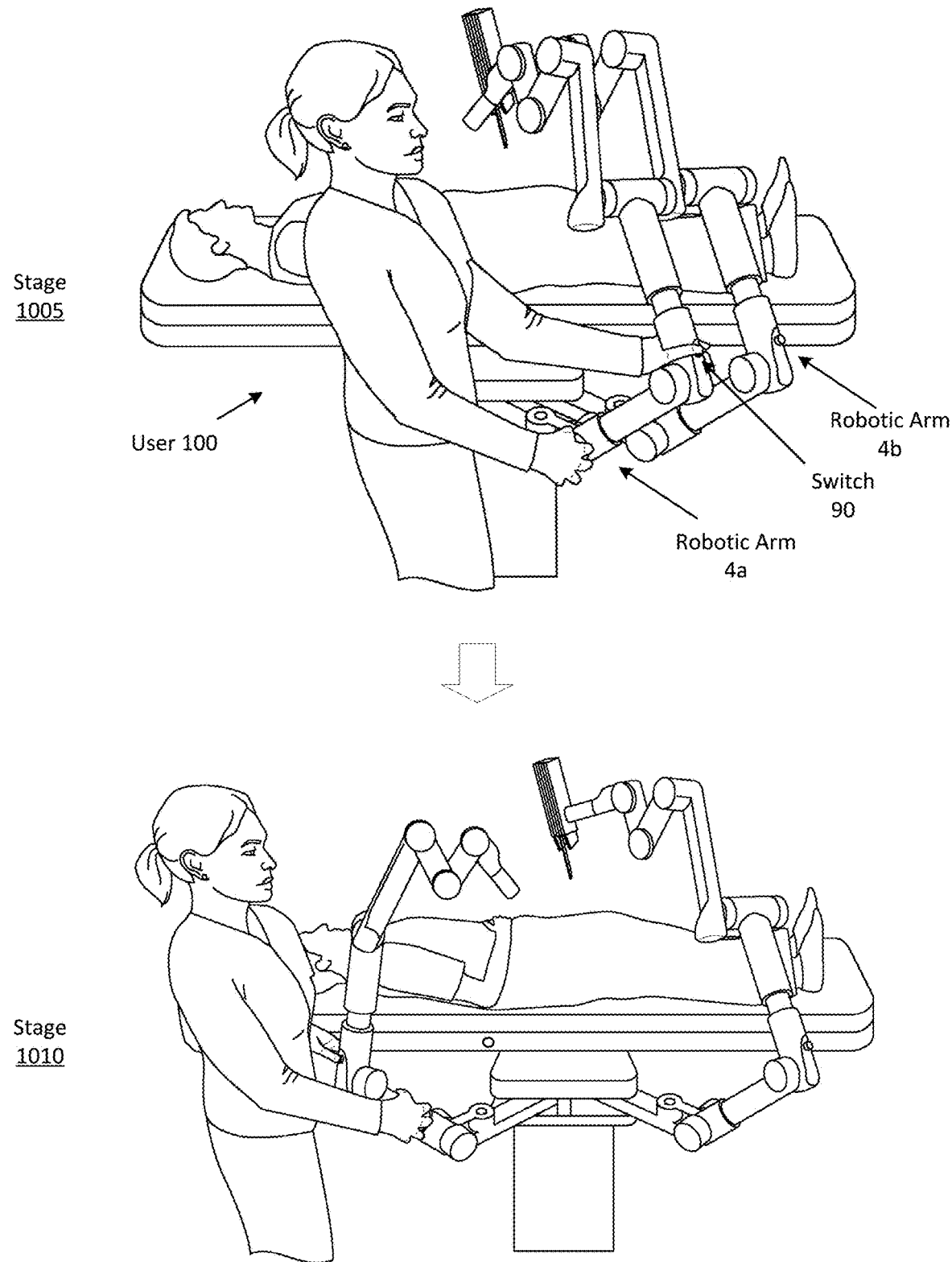
FIG. 10 illustrates several stages of a user moving a robotic arm when a respective user-actuated switch of the arm is actuated by the user according to one embodiment.

FIG. 10 illustrates several stages of a user moving a robotic arm when a respective user-actuated switch of the arm is actuated by the user according to one embodiment. Specifically, this figure illustrates two stages 1005 and 1010 in which a user 100 moves robotic arm 4a from one position to another with respect to the table 5. Stage 1005 illustrates that the user 100 is gripping the robotic arm 4a with her hands and pressing (or actuating) the user-actuated switch 90 down with her thumb. In response, the switch transmits a control signal to the table-side electronics, which uses the signal to determine that the user-actuated switch of the robotic arm has been actuated. Once actuated, the table-side electronics may activate or begin to receive sensor data from one or more sensors, as described herein. Thus, the table-side electronics may receive a signal from the one or more sensors that indicates a direction in which the robotic arm is being forced to move by the user 100. In this case, the sensor data may indicate that the user is pulling the robotic arm 4a away from the robotic arm 4b, and rotating the arm away from the table top. As a result, the table-side electronics may produce one or more joint command signals that cause driving mechanisms of one or more joints of the robotic arm to assist movement of the robotic arm in the direction indicated by the signal. Stage 1010 shows the result of the movement by the user. For instance, the arm 4a has rotated about a vertical axis away from the robotic arm 4b, and is now positioned to the side of the table top.

Figure 11:
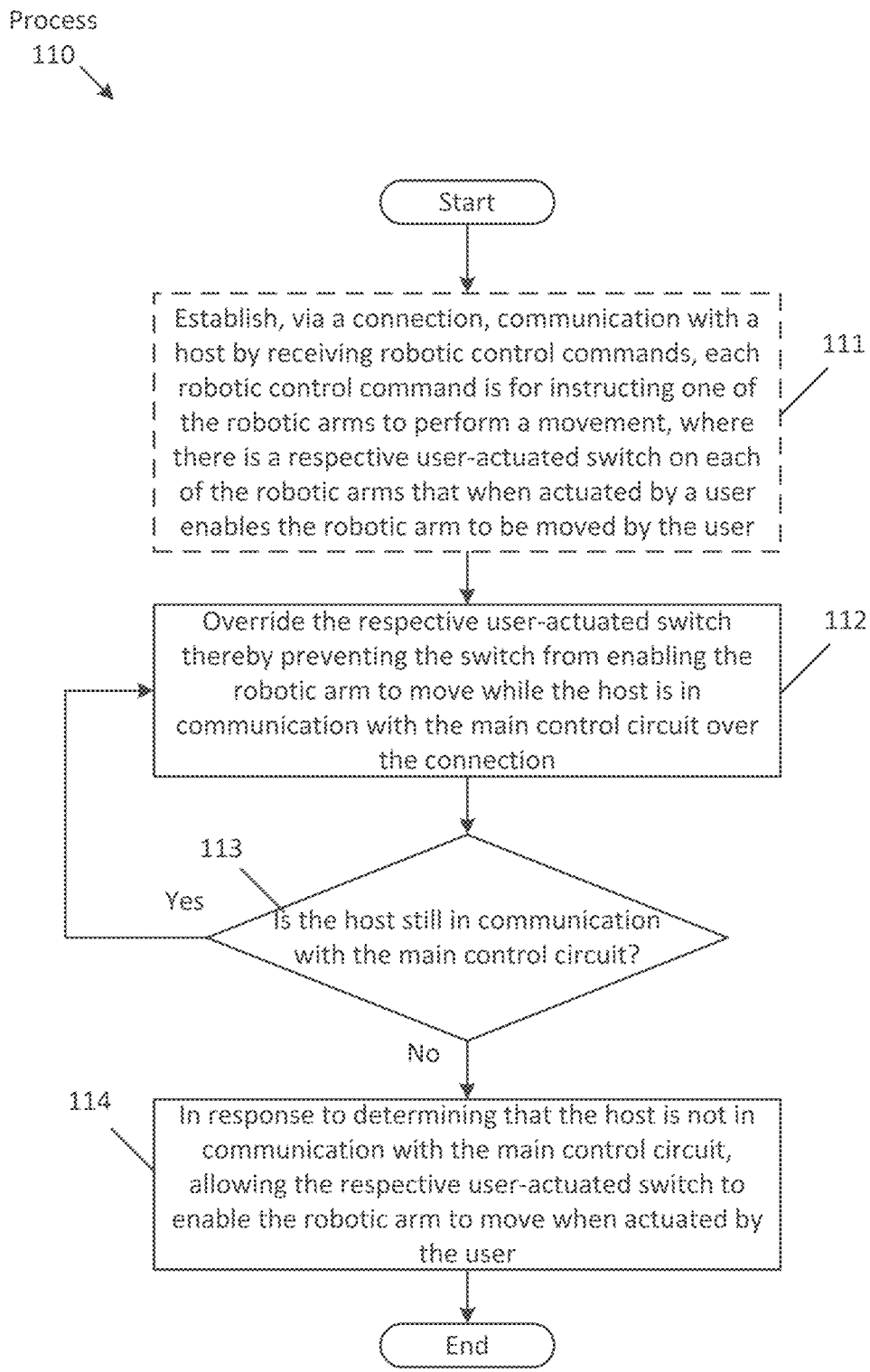
FIG. 11 is a flowchart of one embodiment of a process to allow a user-actuated switch to enable a robotic arm to move when actuated by a user in response to determining that communication between the table-side electronics and a host has ceased according to one embodiment.

FIG. 11 is a flowchart of one embodiment of a process to allow a user-actuated switch to enable a robotic arm to move when actuated by a user in response to determining that communication between table-side electronics and a host has ceased or has been terminated according to one embodiment. Specifically, this process describes the two modes in which the surgical robotic system 1 may operate. This figure will be described with reference to FIGS. 2 and 9. For instance, at least some of the operations described herein may be performed by the (e.g., main control circuit 21 of the table-side electronics 20 of the) surgical robotic system 1. In particular, the operations may be performed by the communication controller that has the master responsibility, as described herein. In another embodiment, at least some of the operations may be performed by another processor (or controller) that is integrated within the system. For example, the robotic arm 4a may include a processor that is configured to determine whether the respective user-actuated switch of the robotic arm is actuated and allow the driving mechanism of the arm to move (e.g., based on a user-applied force).

The process 110 begins by establishing, via a connection, communication with a host by receiving robotic control commands, each robotic control command is for instructing one of the robotic arms to perform a movement, where there is a respective user-actuated switch on each of the robotic arms that when actuated by a user enables the robotic arm to be moved by the user (at block 111). For instance, the communication may be via any communication protocol over any type of connection (e.g., a wired connection or a wireless connection). In one embodiment, the communication may be established at the beginning of a surgical procedure. As a result, when communication is established, the surgical robotic system may be in the teleoperation mode in which the surgical robotic system, namely each of the robotic arms 4a-4n and the table 5 are under full control of the operator via the host 16. Thus, the process 110 overrides (e.g., once communication is established) the respective user-actuated switch thereby preventing the switch from enabling the robotic arm to move (at block 112). Specifically, while in the teleoperation mode the system 1 may not respond to the user-actuated switch 90 of the robotic arms being actuated. For instance, the (communication controller with the master responsibility of the) main control circuit may override the switch while the circuit 21 communicates with the host over the connection. Along with overriding the user-actuated switch 90 of each arm, the system may also override the table user-actuated switch 91 thereby preventing the table-user actuated switch form enabling the surgical table from being adjusted once communication with the host has been established.

In one embodiment, the main control circuit 21 may override the switches while in teleoperation mode in at least one of several methods. In one embodiment, the main control circuit may override the switch by not providing power to the switch, thereby not allowing a control signal to be produced by the switch when actuated by a user. In another embodiment, the controller with the master responsibility may receive a control signal from the switch when actuated, but may ignore the signal while in teleoperation mode. In one embodiment, while in teleoperation mode, the communication controller may not respond by not transmitting joint command signals to driver mechanisms to the robotic arms and/or table in response to sensing that the user (e.g., user 100) is applying a push and/or pull force.

The process 110 determines whether host is still in communication with the main control circuit (at decision block 113). Specifically, the system determines whether a communication connection (or link) between the host and main control circuit is terminated or lost. For example, this determination may be based on whether input data (e.g., robotic command signals) have ceased to be received from the host after a period of time (e.g., five minutes). As another example, the determination may be based on an explicit command from the host indicating that communication has been terminated (e.g., a communication link, such as a BLUETOOTH link has been terminated). In another embodiment, any method may be used to determine whether communication with the host has been lost or terminated by the surgical robotic system 1. If so, the process 110 returns to block 112 to continue overriding the user-actuated switches.

In response to determining that the communication with the host has ceased, however, the process 110 allows the respective user-actuated switch to enable the robotic arm to move when actuated by the user (at block 114). Specifically, once it is determined that communication has ceased, the surgical robotic system switches from teleoperation mode to local mode in order to allow users to manually move the robotic arms and/or table. Thus, as described herein, when a user-actuated switch 90 of a robotic arm is actuated, the communication controller (with the master responsibility) may transmit joint command signals to driver mechanisms in response to receiving sensor data that indicates a direction and/or speed at which the robotic arm is to be moved.

Some embodiments perform variations of the process 50. For example, the specific operations of the process may not be performed in the exact order shown and described. The specific operations may not be performed in one continuous series of operations and different specific operations may be performed in different embodiments. For example, upon determining that communication has been terminated, the surgical robotic system may alert users within the operating room (and the operator). For instance, as described herein, the table-side electronics of the surgical robotic system may include a speaker. In response to determining that communication with the host has been terminated, the system may drive the speaker with an alert message alerting users that communication between the host and the (main control circuit of the) table-side electronics has been terminated.

In one embodiment, at least some of the operations described herein may be optional (illustrated as dashed boxes), and thereby may be omitted from the process. For instance, the process 110 may be performed while the surgical robotic system 1 is already within teleoperation mode (e.g., while the host is communicating with the main control circuit 21). Thus, communication with the host is already established.

In one embodiment, the (e.g., main control circuit 21 of the) table-side electronics may not enable the robotic arm to move in response to the user-actuated switch and/or the table user-actuated switch being actuated under certain conditions, even though the communication has been terminated. For instance, once the user-actuated switch 90 is actuated, the system 1 may determine whether a surgical tool 7 is coupled to the robotic arm. In one embodiment, the main control circuit does not allow the respective user-actuated switch to enable the robotic arm to move unless it has been determined that the surgical tool is not coupled to the robotic arm. For example, the surgical tool 7 that is coupled to the robotic arm 4a may include a sharp object, such as a scalpel or a cannula. If moved while the tool remains coupled to the arm, the tool may inadvertently come into contact with the patient who is still on top of the table 5. Thus, in order to avoid injuring the patient, the system may wait to allow the switch to enable movement until the tool is removed. In one embodiment, so long as a surgical tool is coupled to a robotic arm after determining that communication with the host has been terminated, the system may override the respective user-actuated switch of the robotic arm from enabling the robotic arm to move in response to being actuated by the user. In another embodiment, the system may not override the switch once communication is lost, regardless of whether (or not) the surgical tool is coupled to the robotic arm.

In one embodiment, the (e.g., main control circuit 21 of the) system 1 may wait for a period of time (after switching from the teleoperation mode to the local mode) to allow a user-actuated switch to enable movement of a respective arm after communication has terminated. Specifically, in response to determining that the host has ceased communicating with the main control circuit over a connection (e.g., communication link with the host has been inadvertently terminated), the system enables each of the robotic arms (and the surgical table) to hold a current position in order to avoid any abrupt movement (e.g., an arm collapsing on the patient). In addition, the system may continue to override the respective user-actuated switch from enabling the robotic arm to move for a period of time (e.g., thirty seconds) after it is determined the has ceased. For instance, in cases in which communication is intermittent (e.g., periodically terminating and being reestablished) or is only for a short period of time (e.g., five seconds), the system will wait for the period of time in order to allow the connection to be reestablished.

As described herein, the surgical robotic system 1 may include several controllers, such as the monitoring controller 22, the first communication controller 23, the second communication controller 24, the input power controller 60, the first power controller 63, and the second power controller 64. In one embodiment, each of the controllers described herein may be separate special-purpose processors with respect to one another. For example, each controller may be an application-specific integrated circuit (ASIC), a general purpose microprocessor, a field-programmable gate array (FPGA), a System on Chip (SoC) with one or more processors, a System on Module (SOM), a digital signal controller, or a set of hardware logic structures (e.g., filters, arithmetic logic units, and dedicated state machines). In one embodiment, the controllers may include other electronic components. For example, the monitoring controller 22 may include other electronic components, such as integrated circuits (ICs, such as transistors (or switches)) and memory.

In one embodiment, several aspects of the disclosure may be described as the following statements. For instance, an electronic circuit (e.g., the table-side electronics 20, as described herein) for the surgical robotic system 1, which includes the surgical table (e.g., 5) and one or more robotic arms (e.g., 4a-4n) may include one or more components, as described herein. In one embodiment, the electronic circuit includes a main control circuit (e.g., 21) that is arranged to communication with a host (e.g., 16) over a connection by receiving robotic control commands that are translated by a control computer (e.g., 3) from commands that the control computer receives from the host. Each robotic control command is for instructing one of the robotic arms to perform a movement. Each arm has a respective user-actuated switch (e.g., 90) that when actuated by a user enables the robotic arm to move moved by the user. The main control circuit is configured to 1) override the switch thereby preventing the switch from enabling the robotic arm to move while the host communicates with (or is in communication) with the main control circuit over the connection and 2), in response to determining that the host has ceased communicating with the main control circuit over the connection, allowing the respective user-actuated switch to enable the robotic arm to move when actuated by the user.

In one embodiment, the surgical table includes a table user-actuated switch (e.g., 91) that when actuated by the user enables the surgical table to be adjusted by the user. The main control circuit, however, overrides the table user-actuated switch while the circuit is in communication with the host thereby preventing the switch from enabling the table from being adjusted.

In another embodiment, the robotic arm has a surgical tool (e.g., 7) coupled thereto and the main control circuit does not allow the respective user-actuated switch to enable the robotic arm to move unless the surgical tool is no longer coupled to the robotic arm.

In some embodiment, the main control circuit overrides the respective user-actuated switch of the robotic arm from enabling the arm to move in response to being actuated by the user, so long as a surgical tool is coupled to the robotic arm after determining that the host is no longer communicating with the main control circuit.

In one embodiment, the main control circuit allows the respective user-actuated switch to enable the robotic arm movement by 1) determining that a user-actuated switch of a robotic arm has been actuated, 2) receiving a signal that indicates a direction in which the robotic arm is being forced to move, and 3) causing a driving mechanism of the robotic arm to assist movement of the robotic arm in the direction indicated by the signal. In another embodiment, the main control circuit includes a communication controller configured to route robotic control commands received from the host to the robotic arms and the communication controller causes the driving mechanism of the robotic arm to assist movement by producing and transmitting a robotic control command based on the received signal to the driving mechanism.

In one embodiment, the main control circuit is configured to, in response to determining that the host has ceased communicating with the main control circuit over the connection, 1) enable each of the robotic arms to hold a current position and 2) continue overriding the respective user-actuated switch from enabling the robotic arm to move for a period of time after the communication has ceased.

In another embodiment of the disclosure, a surgical robotic system and a method contain at least some of the components described herein and perform at least some of the processes as described herein.

As previously explained, an embodiment of the disclosure may be a non-transitory machine-readable medium (such as microelectronic memory) having stored thereon instructions, which program one or more data processing components (generically referred to here as a "processor") to perform the network operations, signal processing operations, joint command operations, etc. In other embodiments, some of these operations might be performed by specific hardware components that contain hardwired logic. Those operations might alternatively be performed by any combination of programmed data processing components and fixed hardwired circuit components.

While certain embodiments have been described and shown in the accompanying drawings, it is to be understood that such embodiments are merely illustrative of and not restrictive on the broad disclosure, and that the disclosure is not limited to the specific constructions and arrangements shown and described, since various other modifications may occur to those of ordinary skill in the art. The description is thus to be regarded as illustrative instead of limiting.

In some embodiments, this disclosure may include the language, for example, "at least one of [element A] and [element B]." This language may refer to one or more of the elements. For example, "at least one of A and B" may refer to "A," "B," or "A and B." Specifically, "at least one of A and B" may refer to "at least one of A and at least one of B," or "at least of either A or B." In some embodiments, this disclosure may include the language, for example, "[element A], [element B], and/or [element C]." This language may refer to either of the elements or any combination thereof. For instance, "A, B, and/or C" may refer to "A," "B," "C," "A and B," "A and C," "B and C," or "A, B, and C."

What is claimed is:

1. A surgical robotic system comprising:
   a robotic component; and
   a redundant power architecture that manages and distributes power from a first power source and a second power source to the robotic component, the redundant power architecture comprising:
      a circuit breaker coupled to the first power source, the second power source, and the robotic component,
      a first controller and a second controller, and
      a logic circuit that communicatively couples the circuit breaker to the first controller and the second controller, wherein the redundant power architecture is configured to:
         distribute power from at least one of the first power source and the second power source to the robotic component responsive to one of the first controller and the second controller signaling the logic circuit to cause the circuit breaker to remain closed, and
         cease distribution of power from the at least one of the first power source and the second power source to the robotic component responsive to both of the first controller and the second controller signaling the logic circuit to cause the circuit breaker to open.

2. The surgical robotic system of claim 1 further comprising an input power controller that is electrically coupled between 1) the first power source and the second power source and 2) the redundant power architecture, and is configured select which of the first power source or the second power source is to provide the power to the redundant power architecture responsive to detecting a fault within the surgical robotic system.

3. The surgical robotic system of claim 1, wherein the redundant power architecture further comprises:
   a central power node electrically coupled to the circuit breaker; and
   a first voltage bus that electrically couples the first power source to the central power node and a second voltage bus that electrically couples the second power source to the central power node.

4. The surgical robotic system of claim 3, wherein the circuit breaker is an output circuit breaker, wherein the redundant power architecture further comprises a first input circuit breaker that is electrically coupled between the first voltage bus and the central power node and a second input circuit breaker that is electrically coupled between the second voltage bus and the central power node.

5. The surgical robotic system of claim 3 further comprising a main control circuit that is configured to control the robotic component, while power is distributed by the redundant power architecture.

6. The surgical robotic system of claim 5, wherein the circuit breaker is a first circuit breaker, wherein the redundant power architecture further comprises a second circuit breaker and a third circuit breaker that are both electrically coupled between the central power node and the main control circuit.

7. The surgical robotic system of claim 1 further comprising a surgical table that is arranged to hold a patient, wherein the surgical table comprises the redundant power architecture and the robotic component that is a robotic arm mounted on the surgical table.

8. An electronic circuit for a surgical robotic system that comprises one or more robotic components, the electronic circuit comprising:
   a first voltage bus that is arranged to electrically couple a first power source to a robotic component of the surgical robotic system and a second voltage bus that is arranged to electrically couple a second power source to the robotic component;
   a circuit breaker coupled to the first voltage bus, the second voltage bus, and the robotic component;
   a first controller and a second controller; and
   a logic circuit that communicatively couples the circuit breaker to the first controller and the second controller, wherein the circuit breaker is arranged to:
      provide current from at least one of the first power source and the second power source so long as one of the first controller and the second controller transmits a control signal to the logic circuit which causes the logic circuit to signal the circuit breaker to close, and
      only prevent current from being provided by the first power source and the second power source to flow to the robotic component responsive to each of the first controller and second controller transmitting control signals to the logic circuit to cause the logic circuit to signal the circuit breaker to open.

9. The electronic circuit of claim 8 further comprising an input power controller that is electrically coupled between 1) the first power source and the second power source and 2) the circuit breaker, and is configured select which of the first power source or the second power source is to provide the power to the robotic component responsive to a fault detection.

10. The electronic circuit of claim 8 further comprises a central power node that is electrically coupled between the first voltage bus and the second voltage bus and the circuit breaker.

11. The electronic circuit of claim 10 further comprises a first input circuit breaker that is electrically coupled between the first voltage bus and the central power node and a second input circuit breaker that is electrically coupled between the second voltage bus and the central power node.

12. The electronic circuit of claim 8, wherein the electronic circuit is a part of a surgical table of the surgical robotic system.

13. The electronic circuit of claim 12, wherein the one or more robotic components are robotic arms that are mounted to the surgical table.

14. The electronic circuit of claim 8, wherein the first power source is an alternating current (AC) mains power supply and the second power source is a battery.

15. An electronic circuit for a surgical robotic system comprising:
   a central power node;
   a first voltage bus that is arranged to provide power from a first power source and a second voltage bus that is arranged to provide power from a second power source;

a first input circuit breaker coupled between the first voltage bus and the central power node and a second input circuit breaker coupled between the second voltage bus and the central power node;

a first output circuit breaker coupled between the central power node and a main control circuit that is configured to control a robotic component of the surgical robotic system and a second output circuit breaker coupled between the central power node and the main control circuit; and a plurality of controllers that are communicatively coupled to the first and second input circuit breakers and the first and second output circuit breakers, and are configured to open an input circuit breaker or an output circuit breaker responsive to a detection of an open condition.

16. The electronic circuit of claim 15 further comprising a third output circuit coupled between the central power node and the robotic component.

17. The electronic circuit of claim 15, wherein the input circuit breaker or the output circuit breaker are to open responsive to all of the plurality of controllers transmitting a low control signal to the input circuit breaker or the output circuit breaker.

18. The electronic circuit of claim 15 further comprising a third voltage bus that couples the main control circuit to the first output circuit breaker and a forth voltage bus that couples the main control circuit to the second output circuit breaker, wherein the open condition comprises a fault within at least one of the voltage buses or the main control circuit.

19. The electronic circuit of claim 15, wherein the electronic circuit is a part of a surgical table of the surgical robotic system.

20. The electronic circuit of claim 15, wherein the first power source is an alternating current (AC) mains power supply and the second power source is a battery.

* * * * *